United States Patent
Suzuki et al.

(10) Patent No.: US 11,905,449 B2
(45) Date of Patent: Feb. 20, 2024

(54) COMPOUND, LIQUID CRYSTAL COMPOSITION, CURED PRODUCT, OPTICALLY ANISOTROPIC BODY, AND REFLECTIVE FILM

(71) Applicant: FUJIFILM Corporation, Tokyo (JP)

(72) Inventors: Yuko Suzuki, Minami-ashigara (JP); Keisuke Kodama, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 124 days.

(21) Appl. No.: 17/458,998

(22) Filed: Aug. 27, 2021

(65) Prior Publication Data
US 2021/0388269 A1 Dec. 16, 2021

Related U.S. Application Data

(63) Continuation of application No. PCT/JP2020/005807, filed on Feb. 14, 2020.

(30) Foreign Application Priority Data

Feb. 28, 2019 (JP) .................. 2019-036663

(51) Int. Cl.
| | |
|---|---|
| C09K 19/54 | (2006.01) |
| C07C 15/58 | (2006.01) |
| C07C 43/215 | (2006.01) |
| C07C 69/76 | (2006.01) |
| C07C 69/92 | (2006.01) |
| C07C 211/54 | (2006.01) |
| C07D 321/00 | (2006.01) |
| C07D 321/10 | (2006.01) |
| C09K 19/38 | (2006.01) |
| G02B 5/26 | (2006.01) |

(52) U.S. Cl.
CPC .............. *C09K 19/54* (2013.01); *C07C 15/58* (2013.01); *C07C 43/215* (2013.01); *C07C 69/76* (2013.01); *C07C 69/92* (2013.01); *C07C 211/54* (2013.01); *C07D 321/00* (2013.01); *C07D 321/10* (2013.01); *C09K 19/38* (2013.01); *C07B 2200/05* (2013.01); *C07C 2601/14* (2017.05); *G02B 5/26* (2013.01)

(58) Field of Classification Search
CPC .................................................. C09K 19/52
See application file for complete search history.

(56) References Cited

U.S. PATENT DOCUMENTS

| | | | | |
|---|---|---|---|---|
| 2007/0228325 A1* | 10/2007 | Yumoto | ............... | C09K 19/588 252/299.2 |
| 2018/0030161 A1* | 2/2018 | Takishita | ............... | C09K 19/52 |
| 2021/0072444 A1 | 3/2021 | Muramatsu et al. | | |

FOREIGN PATENT DOCUMENTS

| | | | | |
|---|---|---|---|---|
| CN | 2004-250341 A | | 9/2004 | |
| CN | 106588866 A | * | 4/2017 | ........... C07D 321/10 |
| CN | 107383094 A | | 11/2017 | |
| CN | 107903916 A | | 4/2018 | |
| JP | 2015-200861 A | | 11/2015 | |

OTHER PUBLICATIONS

Cornelis et al. "Chirally Organized Oligothiophenes: Towards Modeling Interchain Interactions Within π-Conjugated Systems", Chemistry—A European Journal, 16(36), pp. 10963-10967 (2010) (Year: 2010).*
Cao et al., "Pd-Catalyzed Asymmetric Allylic Alkylation of Indoles and Pyrroles by Chiral Alkene-Phosphine Ligands," Organic Letters, vol. 13, No. 9, 2011 (Published on Web Apr. 4, 2011), pp. 2164-2167.
Cornelis et al., "Chirally Organized Oligothiophenes Towards Modeling Interchain Interactions Within π-Conjugated Systems," Chemistry European Journals, vol. 16, 2010, pp. 10963-10967.
International Preliminary Report on Patentability and English translation of the Written Opinion of the International Searching Authority (Forms PCT/IB/326, PCT/IB/373 and PCT/ISA/237) for International Application No. PCT/JP2020/005807, dated Sep. 10, 2021.
International Search Report (Form PCT/ISA/210) for International Application No. PCT/JP2020/005807, dated Apr. 28, 2020, with English translation.
Yao et al., "Atroposelective Synthesis of Axially Chiral Biaryls by Palladium-Catalyzed Asymmetric C—H Olefination Enabled by a Transient Chiral Auxiliary," Angewandte Chemie, International Edition, vol. 56, 2017, pp. 6617-6621.
Japanese Office Action for corresponding Japanese Application No. 2021-501940, dated Sep. 6, 2022, with English translation.

\* cited by examiner

*Primary Examiner* — Chanceity N Robinson
(74) *Attorney, Agent, or Firm* — Birch, Stewart, Kolasch & Birch, LLP

(57) ABSTRACT

A compound having an excellent rate of change in HTP caused by exposure is achieved and is represented by General Formula (1). In addition, a composition is formed of the compound, and a cured product, an optically anisotropic body, or a reflective film is obtained by curing the composition.

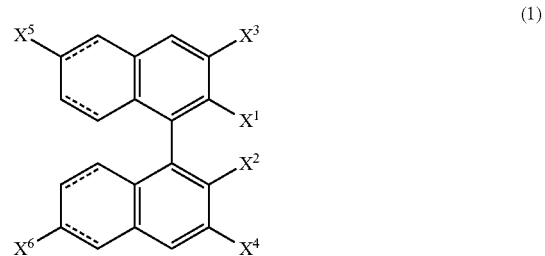

12 Claims, No Drawings

COMPOUND, LIQUID CRYSTAL COMPOSITION, CURED PRODUCT, OPTICALLY ANISOTROPIC BODY, AND REFLECTIVE FILM

CROSS-REFERENCE TO RELATED APPLICATIONS

This application is a Continuation of PCT International Application No. PCT/JP2020/005807 filed on Feb. 14, 2020, which claims priority under 35 U.S.C. § 119(a) to Japanese Patent Application No. 2019-036663 filed on Feb. 28, 2019. Each of the above applications is hereby expressly incorporated by reference, in its entirety, into the present application.

BACKGROUND OF THE INVENTION

1. Field of the Invention

The present invention relates to a compound, a liquid crystal composition, a cured product, an optically anisotropic body, and a reflective film.

2. Description of the Related Art

A compound exhibiting liquid crystallinity (hereinafter, also referred to as a "liquid crystalline compound") can be applied to various uses. For example, the liquid crystalline compound is applied to the manufacturing of an optically anisotropic body typified by a retardation film, or to the manufacturing of a reflective film obtained by immobilizing a cholesteric liquid crystalline phase.

Generally, the cholesteric liquid crystalline phase is formed by adding a chiral compound to a nematic liquid crystal. JP2004-250341A discloses a chiral compound having a helical twisting power (HTP) to the liquid crystalline compound.

SUMMARY OF THE INVENTION

On the other hand, in recent years, there is a demand for a chiral compound which can optionally change HTP by performing a certain treatment. For example, a chiral compound which greatly changes the intensity of HTP caused by exposure to light irradiation such as ultraviolet rays has been desired.

As a result of studies on the chiral compound disclosed in JP2004-250341A, the present inventors have found that, in the chiral compound disclosed in JP2004-250341A, the degree of change in intensity of HTP (hereinafter, also referred to as a "rate of change in HTP) caused by exposure to light irradiation such as ultraviolet rays does not reach the level currently desired.

Therefore, an object of the present invention is to provide a compound having an excellent rate of change in HTP caused by exposure.

Another object of the present invention is to provide a liquid crystal composition formed of the compound, a cured product, an optically anisotropic body, and a reflective film.

The present inventors have found that the above-described objects can be achieved by a compound represented by General Formula (1) described later, and have completed the present invention.

That is, the present inventors have found that the above-described object can be achieved by the following configuration.

[1] A compound represented by General Formula (1) described later.

[2] The compound according to [1], in which, in General Formula (1), $X^1$ and $X^2$ each independently represent the substituent represented by General Formula (2), or
$X^3$ and $X^4$ each independently represent the substituent represented by General Formula (2).

[3] The compound according to [1] or [2], in which, in General Formula (1), $X^3$ and $X^4$ each independently represent the substituent represented by General Formula (2).

[4] The compound according to [1] or [2], in which, in General Formula (1), $X^1$ and $X^2$ each independently represent the substituent represented by General Formula (2).

[5] The compound according to any one of [1] to [4], in which, in General Formula (2), $A^1$ represents an aromatic hydrocarbon ring group.

[6] The compound according to any one of [1] to [5], in which, in General Formula (2), m represents 1 or 2.

[7] The compound according to any one of [1] to [6], in which, in General Formula (1), $X^5$ and $X^6$ each independently represent a substituent represented by General Formula (3) described later.

[8] The compound according to any one of [1] to [7], in which, in General Formula (2), a site represented by $-A^1-(Z^1-A^2)_m-R^1$ and a bonding position represented by *- are arranged in a cis-form in —CH=CH— of General Formula (2).

[9] A liquid crystal composition comprising:
the compound according to any one of [1] to [8]; and
a liquid crystalline compound.

[10] The liquid crystal composition according to [9],
in which the liquid crystalline compound includes two or more polymerizable groups.

[11] A cured product obtained by curing the liquid crystal composition according to [9] or [10].

[12] An optically anisotropic body obtained by curing the liquid crystal composition according to [9] or [10].

[13] A reflective film obtained by curing the liquid crystal composition according to [9] or [10].

According to the present invention, it is possible to provide a compound having an excellent rate of change in HTP caused by exposure.

In addition, according to the present invention, it is possible to provide a liquid crystal composition formed of the compound, a cured product, an optically anisotropic body, and a reflective film.

DESCRIPTION OF THE PREFERRED EMBODIMENTS

Hereinafter, the present invention will be described in detail.

The description of the constitutional requirements described below is made on the basis of representative embodiments of the present invention, but it should not be construed that the present invention is limited to those embodiments.

In the present specification, a numerical range represented using "to" means a range including numerical values described before and after the preposition "to" as a lower limit value and an upper limit value.

In addition, in the present specification, "(meth)acrylate" is a notation representing both acrylate and methacrylate.

In a notation for a group (atomic group) in the present specification, in a case where the group is denoted without specifying whether it is substituted or unsubstituted, the group includes both a group having no substituent and a group having a substituent. For example, "alkyl group" denotes not only an alkyl group having no substituent (unsubstituted alkyl group) but also an alkyl group having a substituent (substituted alkyl group).

In the present specification, in a case of simply referring to a substituent, examples of the substituent include the following substituent T.

(Substituent T)

Examples of the substituent T include a halogen atom (a fluorine atom, a chlorine atom, a bromine atom, an iodine atom, and the like), an alkyl group, a cycloalkyl group, an alkenyl group, a cycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an amino group (including an alkylamino group and an anilino group), an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic thio group, a sulfamoyl group, a sulfo group, an alkyl or arylsulfinyl group, an alkyl or arylsulfonyl group, an acyl group, an aryloxycarbonyl group, an alkoxycarbonyl group, a carbamoyl group, an aryl or heterocyclic azo group, an imido group, a phosphino group, a phosphinyl group, a phosphinyloxy group, a phosphinylamino group, a silyl group, and a group including a polymerizable group (as a suitable specific example, a group represented by General Formula (T)).

*-$L_T$-$P_T$    General Formula (T):

In General Formula (T), $L_T$ represents a single bond or a divalent linking group. $P_T$ represents a polymerizable group represented by General Formulae (P-1) to (P-20) described below.

The divalent linking group represented by $L_T$ is not particularly limited, and an alkylene group which may include a hetero atom is preferable, an alkylene group having 1 to 10 carbon atoms, which may include an oxygen atom, is more preferable, and an alkylene group having 1 to 6 carbon atoms, which may include an oxygen atom, is still more preferable.

In General Formulae (P-1) to (P-20) shown below, * represents a bonding position. In addition, Ra represents a hydrogen atom or a methyl group. In addition, Me represents a methyl group, and Et represents an ethyl group.

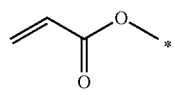
(P-1)

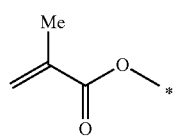
(P-2)

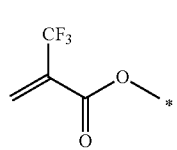
(P-3)

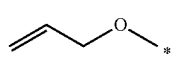
(P-4)

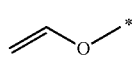
(P-5)

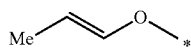
(P-6)

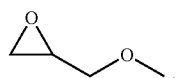
(P-7)

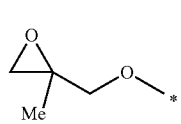
(P-8)

(P-9)

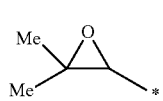
(P-10)

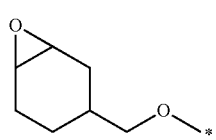
(P-11)

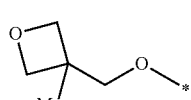
(P-12)

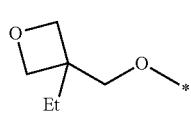
(P-13)

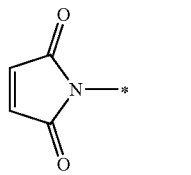
(P-14)

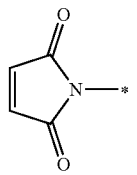
(P-15)

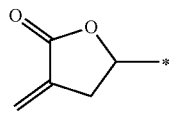
(P-16)

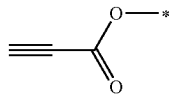
(P-17)

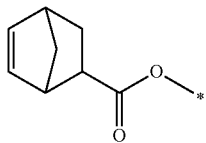
(P-18)

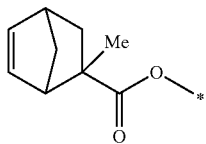
(P-19)

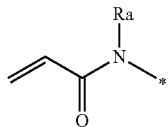
(P-20)

Among the above-described substituents, a substituent having a hydrogen atom may be further substituted with any one of the above-described substituents in the portion of the hydrogen atom in the substituent.

The bonding direction of a divalent group denoted in the present specification is not limited unless otherwise specified. For example, in a compound represented by the General Formula "L-M-N", in a case where M is —OCO—C(CN)=CH—, and the position bonded to the L side is defined as *1 and the position bonded to the N side is defined as *2, M may be *1-OCO—C(CN)=CH—*2 or *1-CH=C(CN)—COO—*2. In addition, for example, in a case where M is —COO—, and the position bonded to the L side is defined as *1 and the position bonded to the N side is defined as *2, M may be *1—COO—*2 or *1—OCO—*2.

[Compound Represented by General Formula (1)]

As a feature of a compound (hereinafter, also referred to as a "specific compound") represented by General Formula (1), at least one of $X^1$, $X^2$, $X^3$, or $X^4$ is a substituent represented by General Formula (2) described later. In other words, the specific compound includes a substituent represented by General Formula (2) described later, so that the specific compound includes, in the molecule, a structural site in which a binaphthyl skeleton (in the present specification, the "binaphthyl skeleton" is intended to a structure other than $X^1$ to $X^6$ of General Formula (1) described later) of General Formula (1) and a group represented by "$A^1$-$(Z^1$-$A^2)_m$-$R^1$" of General Formula (2) are bonded to each other through "—CH=CH—" of General Formula (2). In a case where this structural site is irradiated with energy such as ultraviolet rays, the structural site can be photoisomerized to cause a structural change. Since the specific compound exists in a form in which the structural site capable of causing photoisomerization is directly bonded to the binaphthyl skeleton which is an asymmetric center, it is presumed that the structural change due to the photoisomerization is large and the dihedral angle of the binaphthyl skeleton site is easily changed by the photoisomerization, and as a result, an excellent rate of change in HTP is achieved. For example, in a case where the specific compound has a cis-form structure in which the binaphthyl skeleton of General Formula (1) and the group represented by "-$A^1$-$(Z^1$-$A^2)_m$-$R^1$" of General Formula (2) are arranged in a cis-form in "—CH=CH—" of General Formula (2), the specific compound can be photoisomerized into a trans-form structure in a case of being exposed to energy irradiation such as ultraviolet rays.

As described above, in the present specification, the "binaphthyl skeleton" means a structure (structural site shown below) of General Formula (1) described later, excluding $X^1$ to $X^6$. That is, the "binaphthyl skeleton" generically corresponds to structural sites of General Formula (1-1) and General Formula (1-2) described later, excluding $X^1$ to $X^6$.

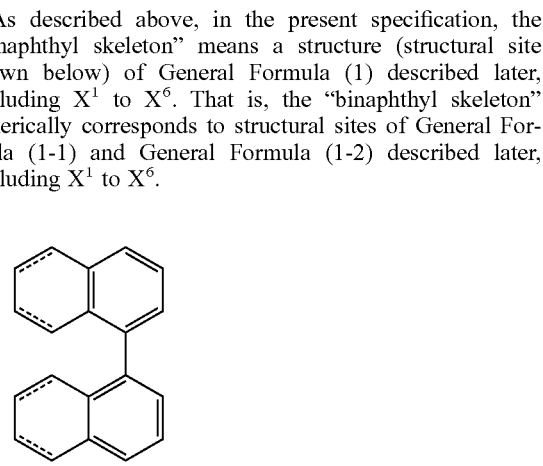

Hereinafter, the specific compound will be described in detail.

The specific compound is a compound represented by General Formula (1).

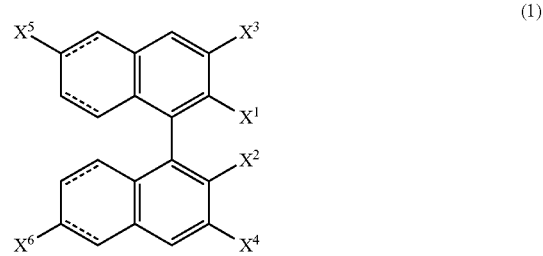
(1)

In General Formula (1), a portion where a solid line and a broken line are parallel to each other represents a single bond or a double bond. For example, in the compound represented by General Formula (1), in a case where the portion where the solid line and the broken line are parallel to each other is a single bond, the compound represented by General Formula (1) corresponds to a compound represented by General Formula (1-1), and in a case where the portion where the solid line and the broken line are parallel to each other is a double bond, the compound represented by General Formula (1) corresponds to a compound represented by General Formula (1-2).

Among these, the specific compound is preferably the compound represented by General Formula (1-2).

$X^1$ to $X^6$ in General Formula (1-1) and General Formula (1-2) respectively have the same meaning as $X^1$ to $X^6$ in General Formula (1).

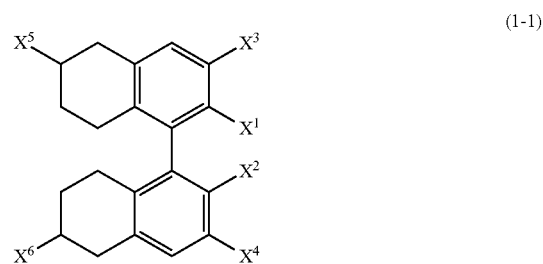
(1-1)

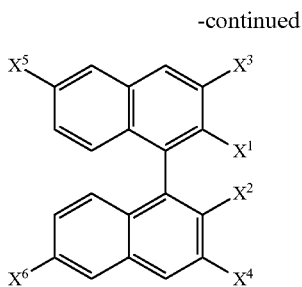

(1-2)

In General Formula (1), $X^1$ to $X^6$ each independently represent a hydrogen atom or a substituent.

The substituent represented by $X^1$ to $X^6$ is not particularly limited, and examples thereof include groups exemplified as the above-described substituent T. However, at least one of $X^1$, $X^2$, $X^3$, or $X^4$ represents a substituent represented by General Formula (2).

(2)

In General Formula (2), $A^1$ and $A^2$ each independently represent a hydrocarbon ring group or a heterocyclic group. $R^1$ represents a hydrogen atom or a substituent. $Z^1$ represents a single bond, —O—, —S—, —CH$_2$O—, —CO—, —COO—, —CO—S—, —O—CO—O—, —CO—NH—, —NR$^A$—, —CH$_2$CH$_2$—, —CH$_2$S—, —CF$_2$O—, —CF$_2$S—, —CH=CH—COO—, —CH=CH—OCO—, —OCO—C(CN)=CH—, —COO—CH$_2$CH$_2$—, —OCO—CH$_2$CH$_2$—, —COO—CH$_2$—, —OCO—CH$_2$—, —CH=CH—, —N=N—, —CH=N—N=CH—, —CF=CF—, —C≡CCOO—, or —C≡C—. $R^A$ represents a hydrogen atom or an alkyl group. m represents an integer of 0 to 2. * represents a bonding position to a binaphthyl skeleton in General Formula (1). In a case where m is 2, a plurality of $Z^1$'s may be the same or different from each other and a plurality of $A^2$'s may be the same or different from each other. In addition, in a case where a plurality of substituents represented by General Formula (2) are present in General Formula (1), the plurality of substituents represented by General Formula (2) may be the same or different from each other.

In General Formula (2), the positional relationship between the group represented by "$A^1$-$(Z^1$-$A^2)_m$-$R^1$" and the bonding position represented by "-*" is not particularly limited, and the positional relationship may be a trans-form (the group represented by "$A^1$-$(Z^1$-$A^2)_m$-$R^1$" and the bonding position represented by "-*" are arranged on the opposite side of the double bond) or a cis-form (the group represented by "$A^1$-$(Z^1$-$A^2)_m$-$R^1$" and the bonding position represented by "-*" are arranged on the same side of the double bond) in "—CH=CH—".

However, the specific compound satisfies all of the following requirements (A) to (C).

Requirement (A): in General Formula (2), in a case where $R^1$ is a substituent represented by —NR$^B$R$^C$, at least one of $R^B$ or $R^C$ represents a hydrogen atom or an alkyl group.

Requirement (B): in a case where two or more of $X^1$ to $X^4$ represent the substituent represented by General Formula (2), a plurality of $R^1$'s do not linked to each other to form a ring, and a plurality of $A^1$'s do not linked to each other to form a ring and a plurality of $A^2$'s do not linked to each other to form a ring.

Requirement (C): in a case where at least one of $X^3$ or $X^4$ is the substituent represented by General Formula (2), $X^1$ and $X^2$ are linked to each other to form a ring.

In a case where the specific compound satisfies the above-described requirement (C), the ring formed by linking $X^1$ and $X^2$ to each other is not particularly limited, and may be either an aromatic ring or a non-aromatic ring, but a non-aromatic ring is preferable.

In a case where $X^1$ and $X^2$ are linked to each other to form a ring, the group to which $X^1$ and $X^2$ are linked to each other is preferably, for example, *-$L^{S1}$-divalent aromatic hydrocarbon ring group-$L^{S2}$-* or *-$L^{S3}$-divalent aliphatic hydrocarbon group -$L^{S4}$-*. * represents a bonding position to the binaphthyl skeleton in General Formula (1).

The above-described aromatic hydrocarbon ring group is not particularly limited, and examples thereof include the same aromatic hydrocarbon ring group exemplified as an example of the hydrocarbon ring group represented by $A^1$ in General Formula (2) described later. Among these, a benzene ring group is preferable.

The above-described aliphatic hydrocarbon group is not particularly limited, and examples thereof include a linear or branched alkylene group having 1 to 6 carbon atoms.

$L^{S1}$ and $L^{S2}$ each independently represent a single bond or a divalent linking group.

The divalent linking group represented by $L^{S1}$ and $L^{S2}$ is not particularly limited, and examples thereof include a divalent aliphatic hydrocarbon group (which may be linear, branched, or cyclic; a divalent aliphatic hydrocarbon group having 1 to 20 carbon atoms is preferable, and examples thereof include an alkylene group, an alkenylene group, and an alkynylene group), —O—, —S—, —SO$_2$—, —NR$^D$—, —CO—, —N=N—, —CH=N—, and a group of a combination of two or more these groups (examples of the group of a combination of two or more groups include —CO—NH—, —CO—S—, —CH$_2$O—, and —COO—). Here, $R^D$ represents a hydrogen atom or an alkyl group (preferably having 1 to 10 carbon atoms).

A hydrogen atom in the above-described divalent linking group may be replaced with another substituent such as a halogen atom.

As $L^{S1}$ and $L^{S2}$, a single bond, a divalent aliphatic hydrocarbon group (which may be linear, branched, or cyclic; a divalent aliphatic hydrocarbon group having 1 to 20 carbon atoms is preferable, and examples thereof include an alkylene group, an alkenylene group, and an alkynylene group), —O—, —CO—, —CO—NH—, —CH$_2$O—, or —COO— is preferable.

$L^{S3}$ and $L^{S4}$ each independently represent a single bond or a divalent linking group.

The divalent linking group represented by $L^{S3}$ and $L^{S4}$ is not particularly limited, and examples thereof include —O—, —S—, —SO$_2$—, —NR$^D$—, —CO—, —N=N—, —CH=N—, and a group of a combination of two or more these groups (examples of the group of a combination of two or more groups include —CO—NH—, —CO—S—, and —COO—). Here, $R^D$ represents a hydrogen atom or an alkyl group (preferably having 1 to 10 carbon atoms).

A hydrogen atom in the above-described divalent linking group may be replaced with another substituent such as a halogen atom.

As $L^{S3}$ and $L^{S4}$, a single bond, —O—, —CO—, —CO—NH—, or —COO— is preferable.

General Formula (1) will be described in detail below.

In General Formula (1), as the substituent represented by $X^1$ to $X^6$, among those described above, the above-described substituent represented by General Formula (2), a substituent represented by General Formula (3) described below, a halogen atom, a hydroxyl group, an alkoxy group, an alkyl group, an acyloxy group, an alkoxycarbonyl group, a phenoxycarbonyl group, a hydrocarbon ring group, or a heterocyclic group is preferable, and the above-described substituent represented by General Formula (2), a substituent represented by General Formula (3) described below, or a halogen atom is more preferable.

$$*-Z^2-(A^3-Z^3)_n-R^2 \quad (3)$$

In General Formula (3), $A^3$ represents a hydrocarbon ring group or a heterocyclic group. $R^2$ represents a substituent. $Z^2$ and $Z^3$ each independently represent a single bond, —O—, —S—, —CH$_2$O—, —CO—, —COO—, —CO—S—, —O—CO—O—, —CO—NH—, —NL$_A$-, —CH$_2$CH$_2$—, —CH$_2$S—, —CF$_2$O—, —CF$_2$S—, —CH=CH—COO—, —CH=CH—OCO—, —OCO—C(CN)=CH—, —COO—CH$_2$CH$_2$—, —OCO—CH$_2$CH$_2$—, —COO—CH$_2$—, —OCO—CH$_2$—, —CH=CH—, —N=N—, —CH=N—N=CH—, —C=N—, —CF=CF—, —C≡C-COO—, or —C≡C—. $L_A$ represents a hydrogen atom or an alkyl group. n represents an integer of 0 to 2. * represents a bonding position to the binaphthyl skeleton in General Formula (1). In a case where n is 2, a plurality of $A^3$'s may be the same or different from each other and a plurality of $Z^3$'s may be the same or different from each other.

In General Formula (1), among these, from the viewpoint that HTP before changing HTP by exposure (hereinafter, also referred to as an "initial HTP") is more excellent, and/or the rate of change in HTP is more excellent, it is preferable that both $X^1$ and $X^2$ represent the above-described substituent represented by General Formula (2) or both $X^3$ and $X^4$ represent the above-described substituent represented by General Formula (2) (in General Formula (1), in a case where both $X^3$ and $X^4$ represent the above-described substituent represented by General Formula (2), as described in the above requirement (C), $X^1$ and $X^2$ are linked to each other to form a ring), and it is more preferable that both $X^1$ and $X^2$ represent the above-described substituent represented by General Formula (2).

In addition, in General Formula (1), in a case where $X^5$ and $X^6$ represent a substituent, the above-described substituent represented by General Formula (3) is preferable as the substituent. Among these, from the viewpoint that the initial HTP is more excellent, it is more preferable that both $X^5$ and $X^6$ represent the above-described substituent represented by General Formula (3).

Next, the above-mentioned General Formula (2) will be described in detail below.

In General Formula (2), $A^1$ and $A^2$ each independently represent a hydrocarbon ring group or a heterocyclic group.

Examples of the hydrocarbon ring group include an aliphatic hydrocarbon ring group and an aromatic hydrocarbon ring group. The number of ring members of a hydrocarbon ring constituting the hydrocarbon ring group is not particularly limited, but is preferably 5 to 10.

The aliphatic hydrocarbon ring constituting the aliphatic hydrocarbon ring group may have a monocyclic structure or a polycyclic structure. In a case where the aliphatic hydrocarbon ring has a polycyclic structure, it is preferable that at least one of the rings included in the polycyclic structure is a 5- or higher membered ring.

The number of carbon atoms in the above-described aliphatic hydrocarbon ring is not particularly limited, but is preferably 5 to 10 and more preferably 5 or 6. Specific examples of the aliphatic hydrocarbon ring include a cyclopentane ring, a cyclohexane ring, a cycloheptane ring, a cyclooctane ring, a norbornene ring, and an adamantane ring. Among these, a cyclopentane ring or a cyclohexane ring is preferable.

The aromatic hydrocarbon ring constituting the aromatic hydrocarbon ring group may have a monocyclic structure or a polycyclic structure. In a case where the aromatic hydrocarbon ring has a polycyclic structure, it is preferable that at least one of the rings included in the polycyclic structure is a 5- or higher membered ring.

The number of carbon atoms in the above-described aromatic hydrocarbon ring is not particularly limited, but is preferably 6 to 18 and more preferably 6 to 10. Specific examples of the aromatic hydrocarbon ring include a benzene ring, a naphthalene ring, an anthracene ring, a phenanthrene ring, and a fluorene ring. Among these, a benzene ring or a naphthalene ring is preferable, and a benzene ring is more preferable.

Examples of the heterocyclic group include an aliphatic heterocyclic group and an aromatic heterocyclic group. The number of ring members of a hetero ring constituting the heterocyclic group is not particularly limited, but is usually 5 to 10.

The aliphatic hetero ring constituting the aliphatic heterocyclic group may have a monocyclic structure or a polycyclic structure. In a case where the aliphatic heterocyclic ring has a polycyclic structure, it is preferable that at least one of the rings included in the polycyclic structure is a 5- or higher membered ring.

Examples of a hetero atom included in the above-described aliphatic hetero ring include a nitrogen atom, an oxygen atom, and a sulfur atom. The number of ring members in the above-described aliphatic hetero ring is not particularly limited, but is preferably 5 to 10. Specific examples of the above-described aliphatic hetero ring include an oxolane ring, an oxane ring, a piperidine ring, and a piperazine ring. In the aliphatic hetero ring, —CH$_2$- constituting the ring may be replaced with —CO—, and examples thereof include a phthalimide ring.

The aromatic hetero ring constituting the aromatic heterocyclic group may have a monocyclic structure or a polycyclic structure. In a case where the aromatic heterocyclic ring has a polycyclic structure, it is preferable that at least one of the rings included in the polycyclic structure is a 5- or higher membered ring.

Examples of a hetero atom included in the above-described aromatic heterocyclic group include a nitrogen atom, an oxygen atom, and a sulfur atom. The number of ring members in the above-described aromatic hetero ring is not particularly limited, but is preferably 5 to 10. Specific examples of the above-described aromatic hetero ring include a pyridine ring, a pyridazine ring, a pyrimidine ring, a pyrazine ring, a triazine ring, a thiophene ring, a thiazole ring, and an imidazole ring.

The hydrocarbon ring group and heterocyclic group represented by $A^1$ and $A^2$ have a structure in which two hydrogen atoms are removed from the hydrocarbon ring and the hetero ring.

The hydrocarbon ring group and heterocyclic group represented by $A^1$ and $A^2$ may further have a substituent. The substituent is not particularly limited, and examples thereof include groups exemplified as the above-described substituent T.

In General Formula (2), as $A^1$, the aromatic hydrocarbon ring group or the aromatic heterocyclic group is preferable, the aromatic hydrocarbon ring group is more preferable, a benzene ring group or a naphthalene ring group is still more preferable, and a benzene ring group is particularly preferable. In a case where $A^1$ is the aromatic hydrocarbon ring group or the aromatic heterocyclic group, the specific compound has a longer conjugation length including the binaphthyl skeleton in General Formula (1), and as a result, the absorption efficiency of long-wavelength light (particularly light having a wavelength of 365 nm) is improved, the photoisomerization is likely to occur in a case of being exposed, and the rate of change in HTP is more excellent.

The aromatic hydrocarbon ring group or the aromatic heterocyclic group represented by $A^1$ may further have a substituent. The substituent is not particularly limited, and examples thereof include groups exemplified as the above-described substituent T.

In General Formula (2), $R^1$ represents a hydrogen atom or a substituent.

The substituent represented by $R^1$ is not particularly limited, and examples thereof include groups exemplified as the above-described substituent T. However, as described above, in General Formula (2), in a case where $R^1$ is a substituent represented by $-NR^BR^C$, at least one of $R^B$ or $R^C$ represents a hydrogen atom or an alkyl group. The above-described alkyl group represented by $R^B$ and $R^C$ may be linear, branched, or cyclic. In addition, the number of carbon atoms thereof is, for example, 1 to 10, preferably 1 to 6. In a case where $R^B$ and $R^C$ each independently represent a substituent other than the alkyl group, examples of the substituent include groups exemplified as the above-described substituent T.

As the substituent represented $R^1$, among these, a halogen atom, a cyano group, a nitro group, a hydroxyl group, an alkoxy group, an alkyl group, an acyloxy group, an alkoxycarbonyl group, a phenoxycarbonyl group, a hydrocarbon ring group, a heterocyclic group, $-NR^BR^C$ ($R^B$ and $R^C$ each independently represent a hydrogen atom or an alkyl group, and suitable aspects are as described above), or the above-described group represented by General Formula (T) is preferable.

The definitions of hydrocarbon ring group and heterocyclic group as the substituent represented by $R^1$ are the same as the definitions of hydrocarbon ring group and heterocyclic group described in $A^1$.

In General Formula (2), $Z^1$ represents a single bond, $-O-$, $-S-$, $-CH_2O-$, $-CO-$, $-COO-$, $-CO-S-$, $-O-CO-O-$, $-CO-NH-$, $-NR^4-$, $-CH_2CH_2-$, $-CH_2S-$, $-CF_2O-$, $-CF_2S-$, $-CH=CH-COO-$, $-CH=CH-OCO-$, $-OCO-C(CN)=CH-$, $-COO-CH_2CH_2-$, $-OCO-CH_2CH_2-$, $-COO-CH_2-$, $-OCO-CH_2-$, $-CH=CH-$, $-N=N-$, $-CH=N-N=CH-$, $-C=N-$, $-CF=CF-$, $-C\equiv C-COO-$, or $-C\equiv C-$.

$R^4$ represents a hydrogen atom or an alkyl group.

The above-described alkyl group represented by $R^4$ may be linear, branched, or cyclic. The number of carbon atoms in the alkyl group represented by $R^4$ is, for example, 1 to 10, preferably 1 to 6.

As $Z^1$, among these, a single bond, $-COO-$, $-CO-NH-$, $-CH=CH-COO-$, or $-C\equiv C-$ is preferable, and a single bond, $-COO-$, or $-CH=CH-COO-$ is more preferable.

In General Formula (2), m represents an integer of 0 to 2.

As m, among these, 1 or 2 is preferable. In a case where m is 1 or 2, since the interaction between the specific compound and a liquid crystalline compound is more excellent, the initial HTP is even more excellent.

In General Formula (2), * represents a bonding position to the binaphthyl skeleton in General Formula (1).

In General Formula (2), in a case where m is 2, a plurality of $Z^1$'s may be the same or different from each other and a plurality of $A^2$'s may be the same or different from each other.

In addition, in a case where a plurality of substituents represented by General Formula (2) are present in General Formula (1), the plurality of substituents represented by General Formula (2) may be the same or different from each other.

In addition, in General Formula (2), from the viewpoint that the rate of change in HTP is more excellent, it is preferable that the positional relationship between the group represented by "$-A^1-(Z^1-A^2)_m-R^1$" and the bonding position represented by "-*" is a cis-form.

Next, the above-mentioned General Formula (3) will be described in detail below.

In General Formula (3), $A^3$ represents a hydrocarbon ring group or a heterocyclic group. The hydrocarbon ring group or the heterocyclic group represented by $A^3$ has the same meaning as the hydrocarbon ring group or the heterocyclic group represented by $A^1$ in General Formula (1), and suitable aspects are also the same.

In General Formula (3), $R^2$ represents a substituent.

The substituent represented by $R^2$ is not particularly limited, and examples thereof include groups exemplified as the above-described substituent T. Among these, a halogen atom, a cyano group, a nitro group, a hydroxyl group, an alkoxy group, an alkyl group, an acyloxy group, an alkoxycarbonyl group, a phenoxycarbonyl group, a hydrocarbon ring group, or a heterocyclic group is preferable.

The definitions of hydrocarbon ring group and heterocyclic group as the substituent represented by $R^2$ are the same as the definitions of hydrocarbon ring group and heterocyclic group described in $A^1$.

In General Formula (3), $Z^2$ and $Z^3$ each independently represent a single bond, $-O-$, $-S-$, $-CH_2O-$, $-CO-$, $-COO-$, $-CO-S-$, $-O-CO-O-$, $-CO-NH-$, $-NL_A-$, $-CH_2CH_2-$, $-CH_2S-$, $-CF_2O-$, $-CF_2S-$, $-CH=CH-COO-$, $-CH=CH-OCO-$, $-OCO-C(CN)=CH-$, $-COO-CH_2CH_2-$, $-OCO-CH_2CH_2-$, $-COO-CH_2-$, $-OCO-CH_2-$, $-CH=CH-$, $-N=N-$, $-CH=N-N=CH-$, $-C=N-$, $-CF=CF-$, $-C\equiv C-COO-$, or $-C\equiv C-$.

$L_A$ represents a hydrogen atom or an alkyl group.

The above-described alkyl group represented by $L_A$ may be linear, branched, or cyclic. The number of carbon atoms in the alkyl group represented by $L_A$ is, for example, 1 to 10, preferably 1 to 6.

As $Z^2$ and $Z^3$, among these, a single bond, $-COO-$, $-CH=CH-COO-$, $-CH=CH-$, or $-C\equiv C-$ is preferable, a single bond, $-COO-$, $-CH=CH-$, or $-CH=CH-COO-$ is more preferable, and a single bond or $-CH=CH-$ is still more preferable.

n represents an integer of 0 to 2.

As n, among these, 1 or 2 is preferable.

* represents a bonding position to the binaphthyl skeleton in General Formula (1).

In a case where n is 2, a plurality of $A^3$'s may be the same or different from each other and a plurality of $Z^3$'s may be the same or different from each other.

In addition, in a case where a plurality of substituents represented by General Formula (3) are present in General Formula (1), the plurality of substituents represented by General Formula (3) may be the same or different from each other.

As the specific compound, from the viewpoint that the initial HTP is more excellent, and/or the rate of change in HTP is more excellent, among these, a compound represented by General Formula (1-1X) or a compound represented by General Formula (1-1Y) is preferable.

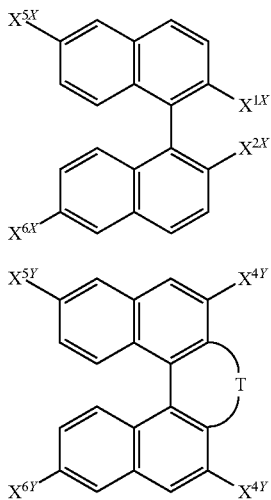

(1-1X)

(1-1Y)

In General Formula (1-1X), $X^{1X}$ and $X^{2X}$ each independently represent the above-described substituent represented by General Formula (2).

$X^{5X}$ and $X^{6X}$ each independently represent a hydrogen atom or the above-described substituent represented by General Formula (3), and it is preferable that both represent the above-described substituent represented by General Formula (3).

In General Formula (1-1Y), $X^{3Y}$ and $X^{4Y}$ each independently represent the above-described substituent represented by General Formula (2).

$X^{5Y}$ and $X^{6Y}$ each independently represent a hydrogen atom or the above-described substituent represented by General Formula (3), and it is preferable that both represent the above-described substituent represented by General Formula (3).

T represents a linking group. As the linking group represented by T, *-$L^{S1}$-divalent aromatic hydrocarbon ring group-$L^{S2}$-* or *-$L^{S3}$-divalent aliphatic hydrocarbon group-$L^{S4}$-* is preferable. * represents a bonding position to a binaphthyl skeleton in General Formula (1-1X) or General Formula (1-1Y).

The above-described aromatic hydrocarbon ring group is not particularly limited, and examples thereof include the same aromatic hydrocarbon ring group exemplified as an example of the hydrocarbon ring group represented by $A^1$ in General Formula (2) described later. Among these, a benzene ring group is preferable.

The above-described aliphatic hydrocarbon group is not particularly limited, and examples thereof include a linear or branched alkylene group having 1 to 6 carbon atoms.

$L^{S1}$ and $L^{S2}$ each independently represent a single bond or a divalent linking group.

The divalent linking group represented by $L^{S1}$ and $L^{S2}$ is not particularly limited, and examples thereof include a divalent aliphatic hydrocarbon group (which may be linear, branched, or cyclic; a divalent aliphatic hydrocarbon group having 1 to 20 carbon atoms is preferable, and examples thereof include an alkylene group, an alkenylene group, and an alkynylene group), —O—, —S—, —SO$_2$—, —NR$^D$—, —CO—, —N=N—, —CH=N—, and a group of a combination of two or more these groups (examples of the group of a combination of two or more groups include —CO—NH—, —CO—S—, —CH$_2$O—, and —COO—). Here, R$^D$ represents a hydrogen atom or an alkyl group (preferably having 1 to 10 carbon atoms).

A hydrogen atom in the above-described divalent linking group may be replaced with another substituent such as a halogen atom.

As $L^{S1}$ and $L^{S2}$, a single bond, a divalent aliphatic hydrocarbon group (which may be linear, branched, or cyclic; a divalent aliphatic hydrocarbon group having 1 to 20 carbon atoms is preferable, and examples thereof include an alkylene group, an alkenylene group, and an alkynylene group), —O—, —CO—, —CO—NH—, —CH$_2$O—, or —COO— is preferable.

$L^{S3}$ and $L^{S4}$ each independently represent a single bond or a divalent linking group.

The divalent linking group represented by $L^{S3}$ and $L^{S4}$ is not particularly limited, and examples thereof include —O—, —S—, —SO$_2$—, —NR$^D$—, —CO—, —N=N—, —CH=N—, and a group of a combination of two or more these groups (examples of the group of a combination of two or more groups include —CO—NH—, —CO—S—, and —COO—). Here, R$^D$ represents a hydrogen atom or an alkyl group (preferably having 1 to 10 carbon atoms).

A hydrogen atom in the above-described divalent linking group may be replaced with another substituent such as a halogen atom.

As $L^{S3}$ and $L^{S4}$, a single bond, —O—, —CO—, —CO—NH—, or —COO— is preferable.

The specific compound can be synthesized by a known method.

The specific compound may be an R-form or an S-form, or may be a mixture of R-form and S-form.

Specific examples of the specific compound will be shown below, but the specific compound is not limited thereto.

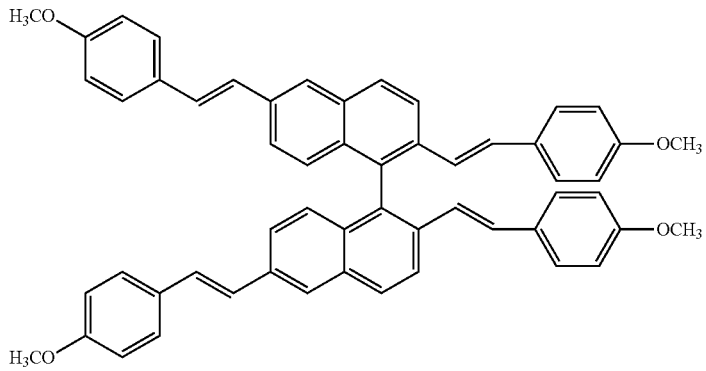

-continued
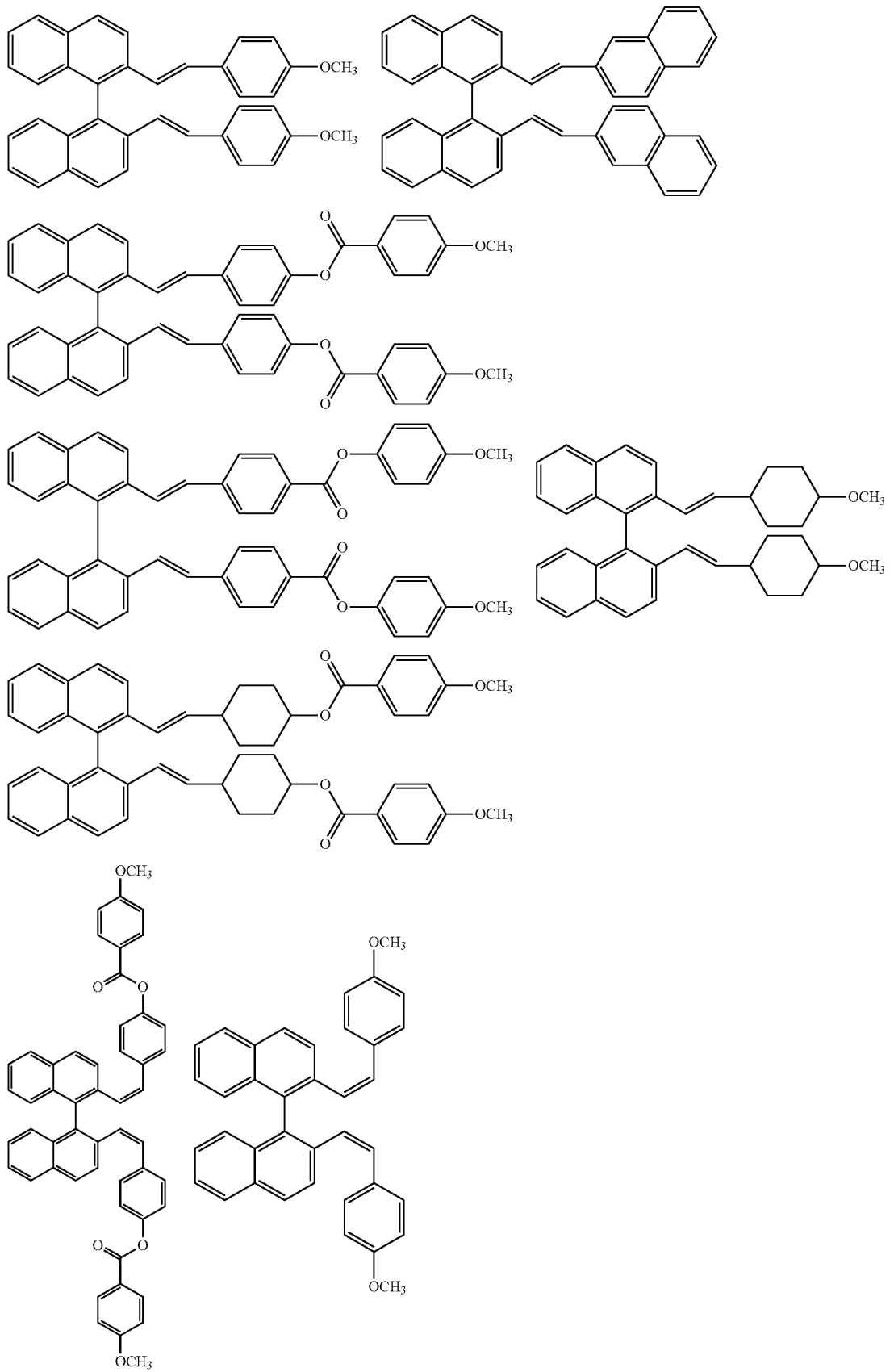

-continued
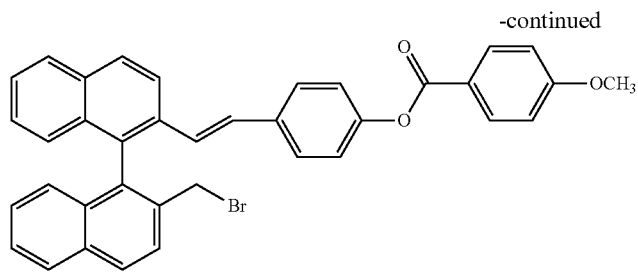
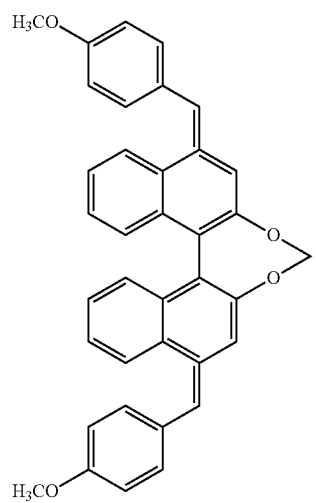
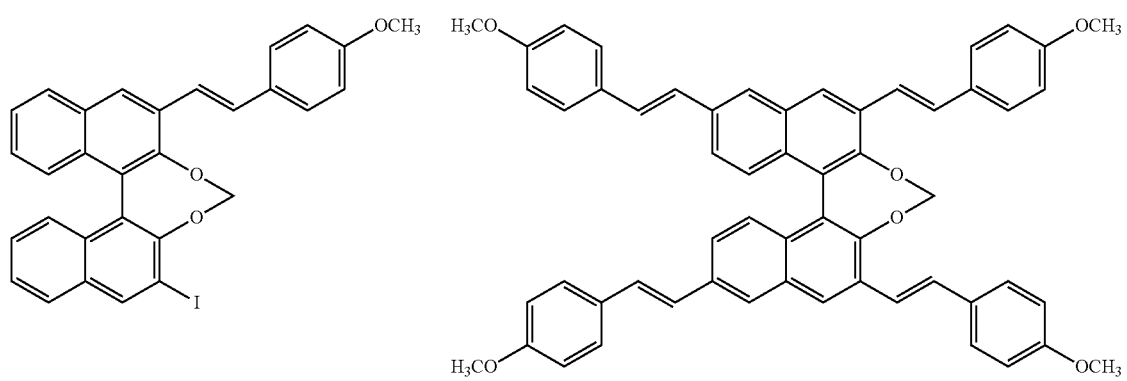
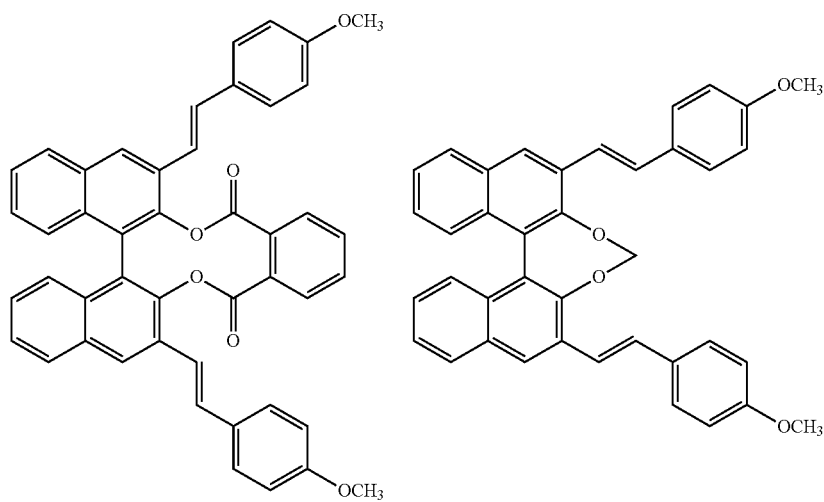

-continued
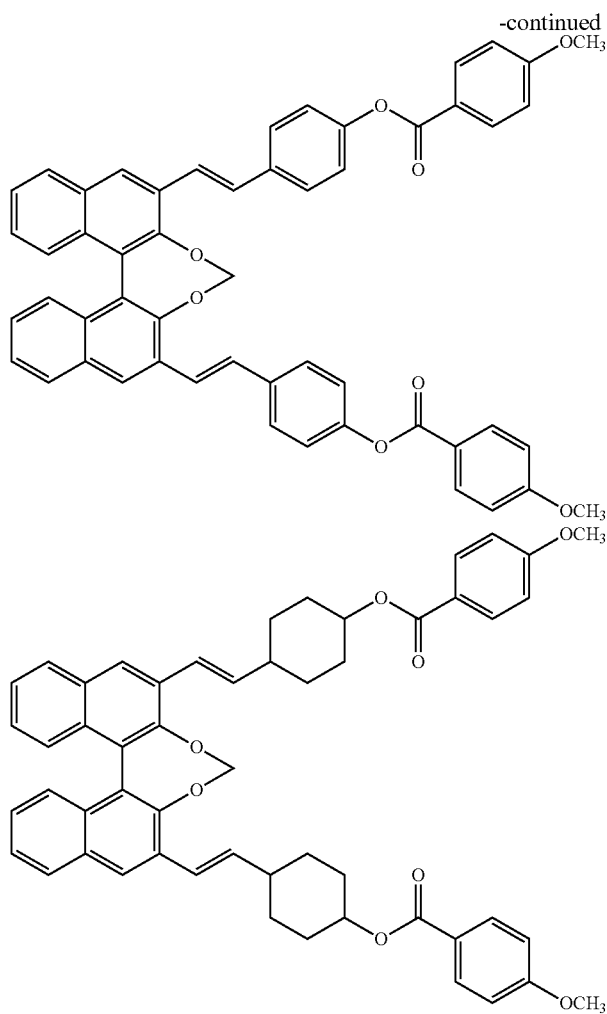
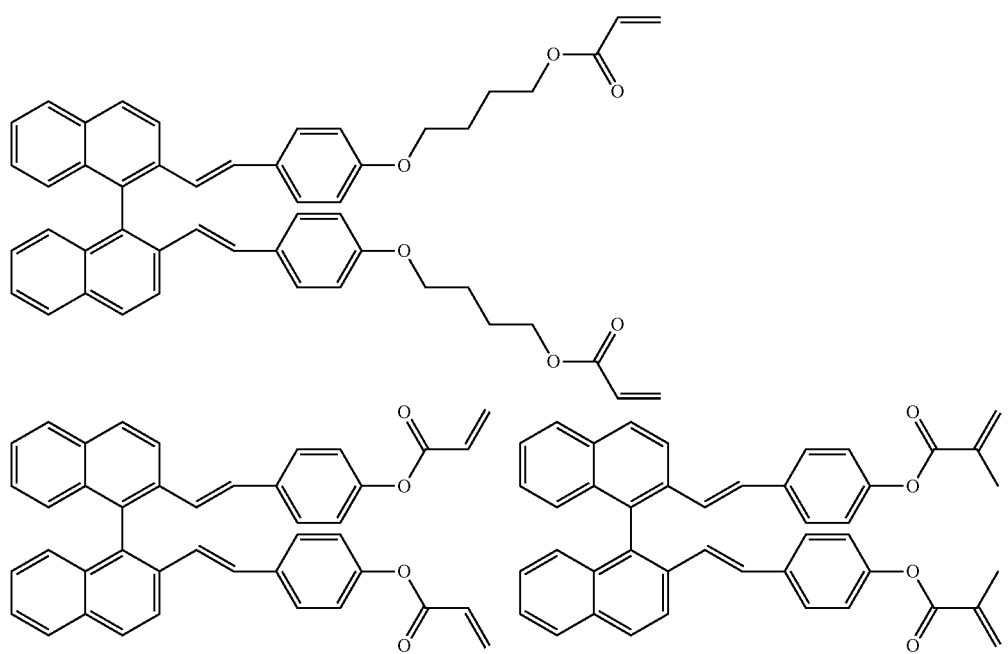

21 22
-continued
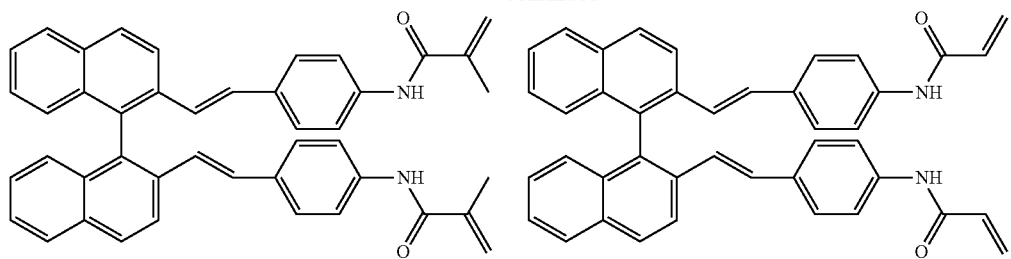
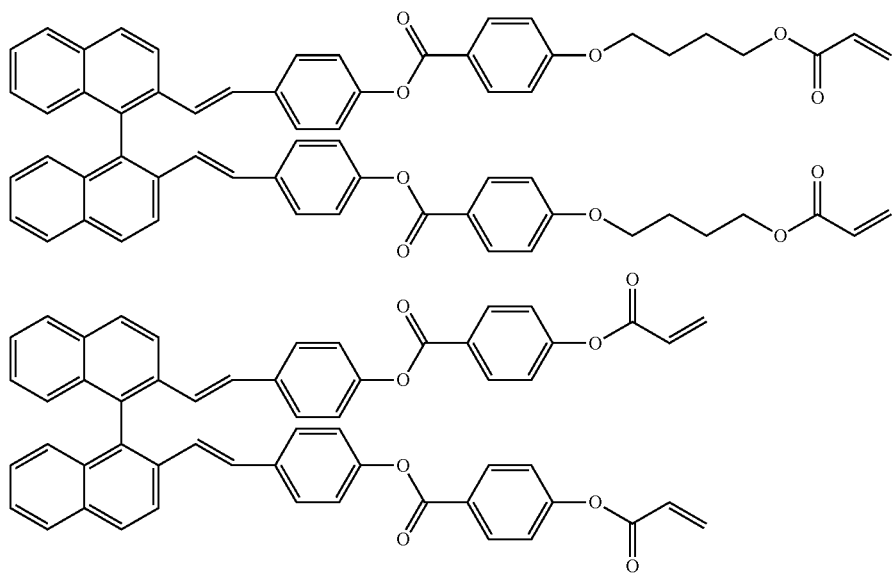
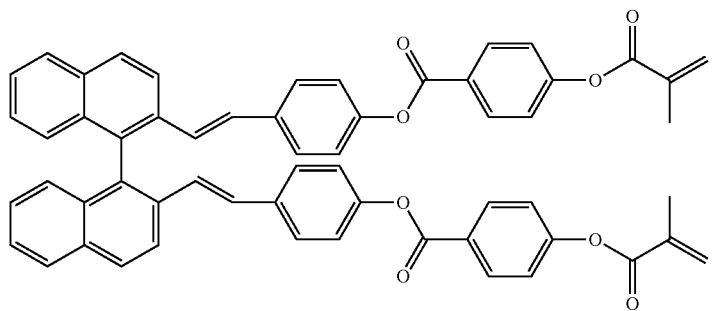
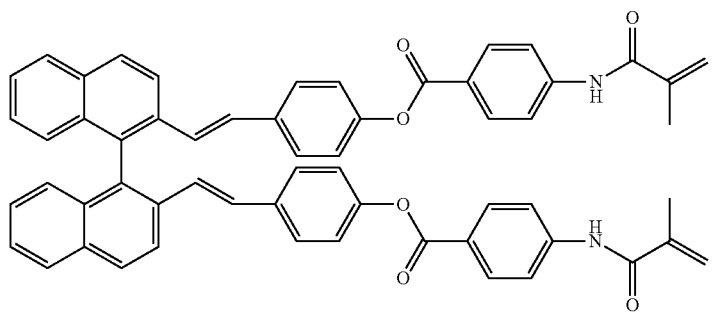

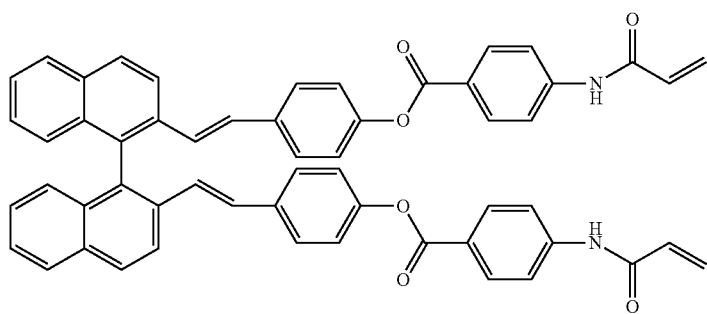
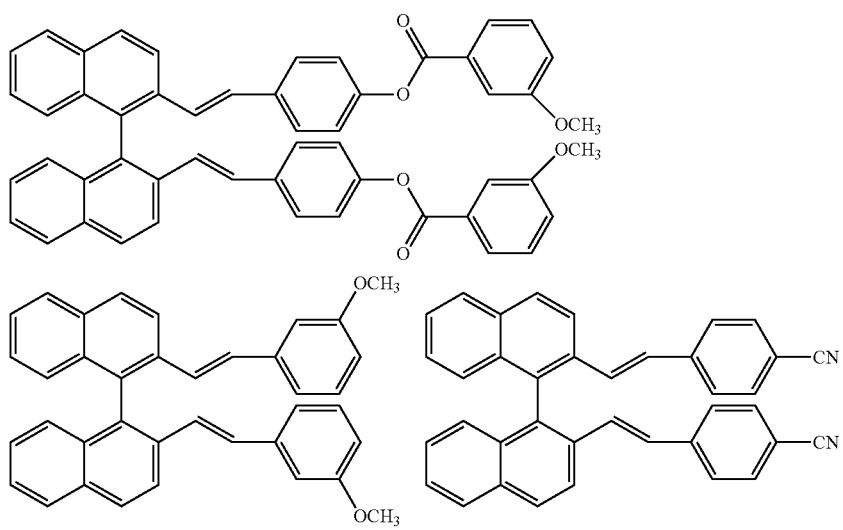
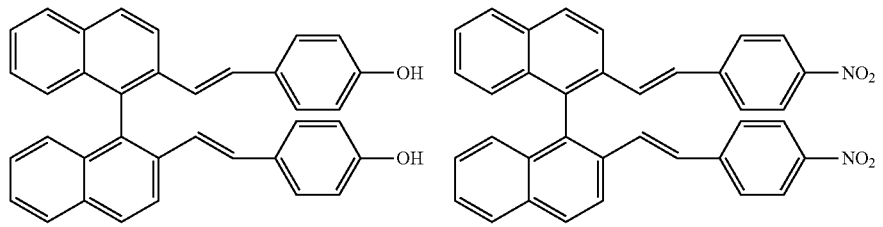
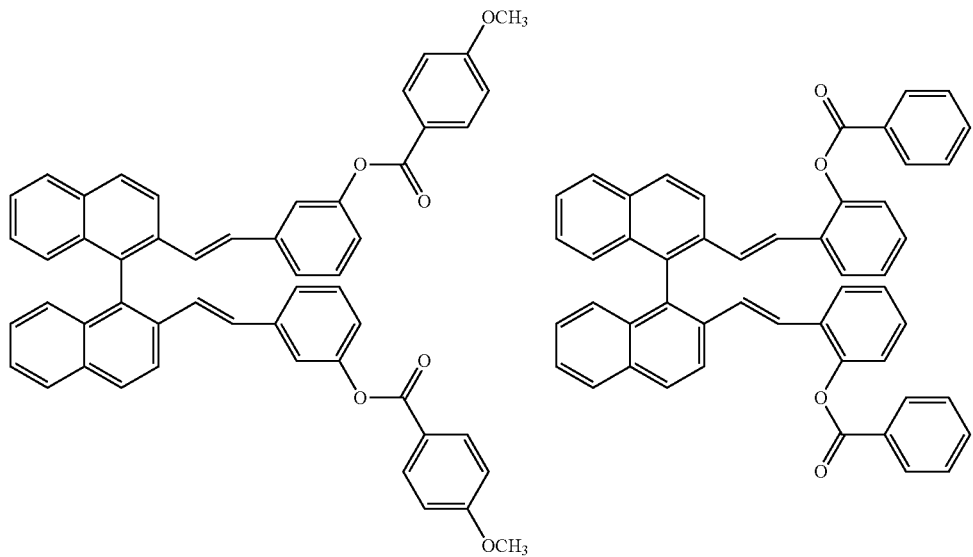

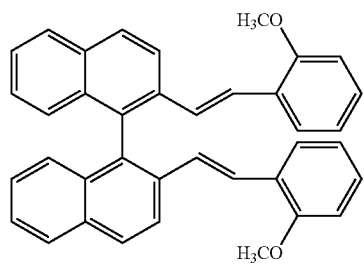
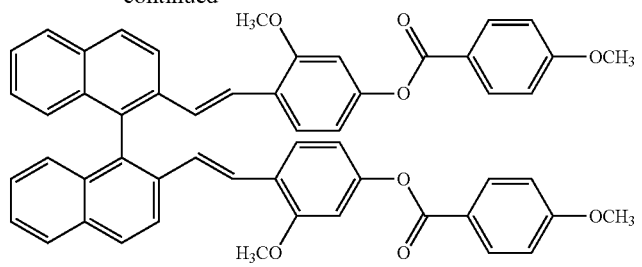
-continued
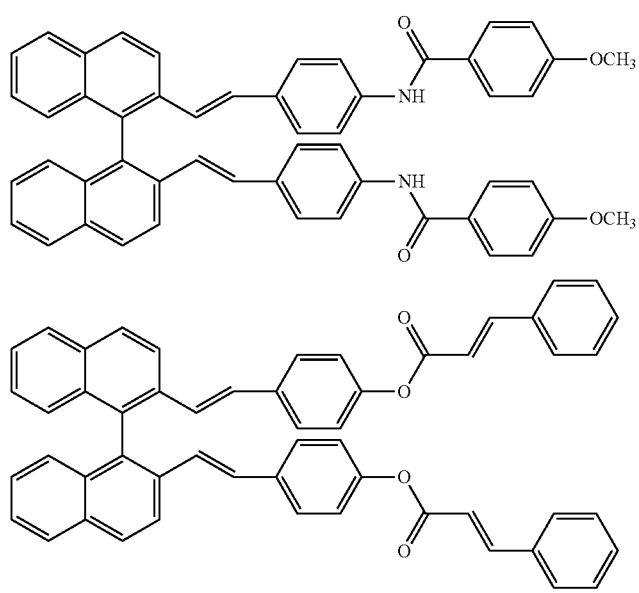
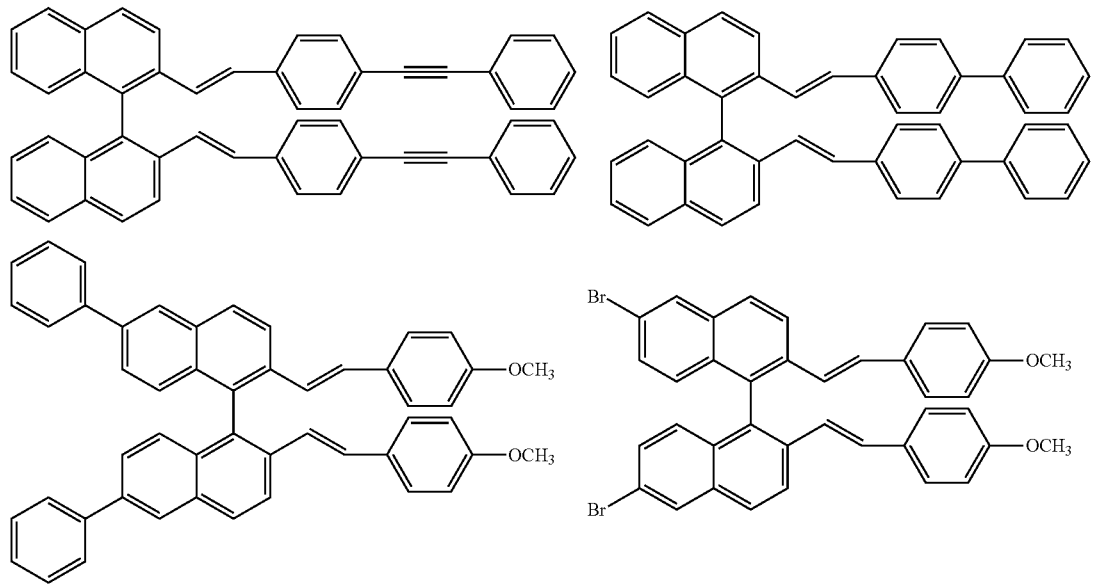

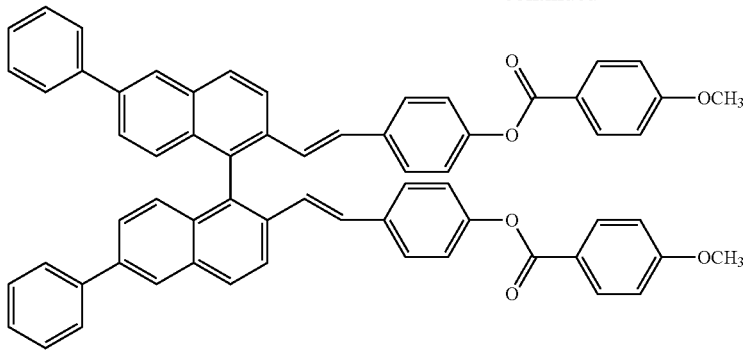
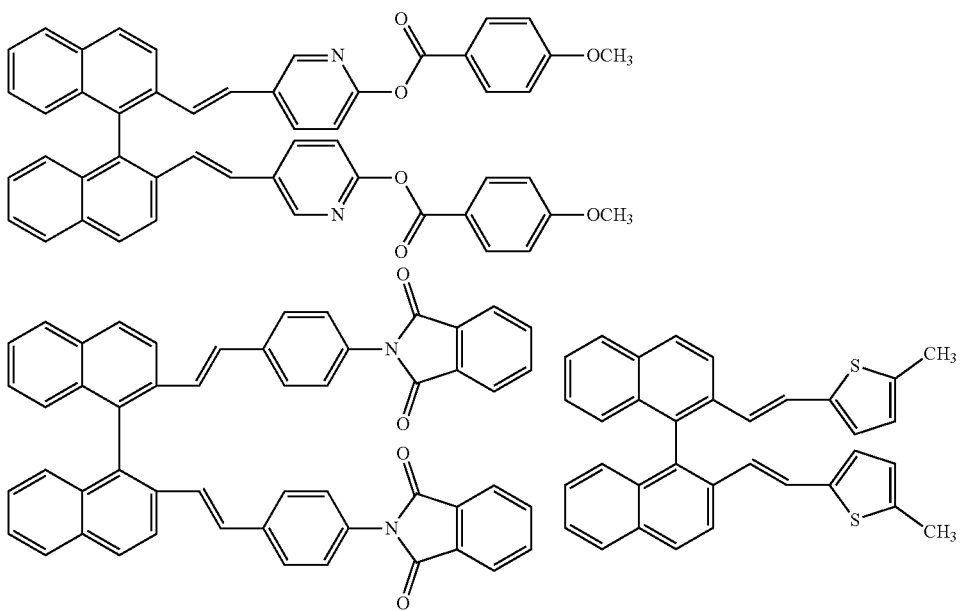
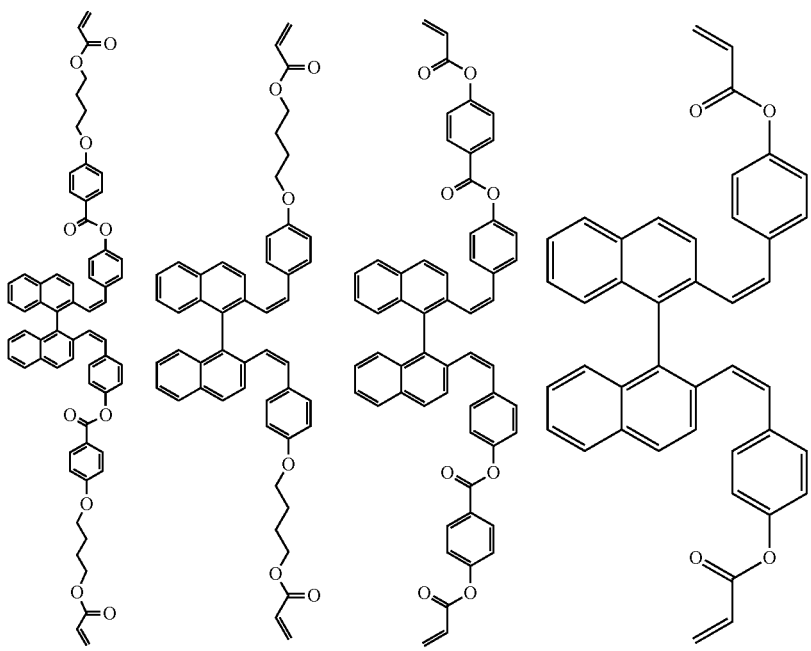

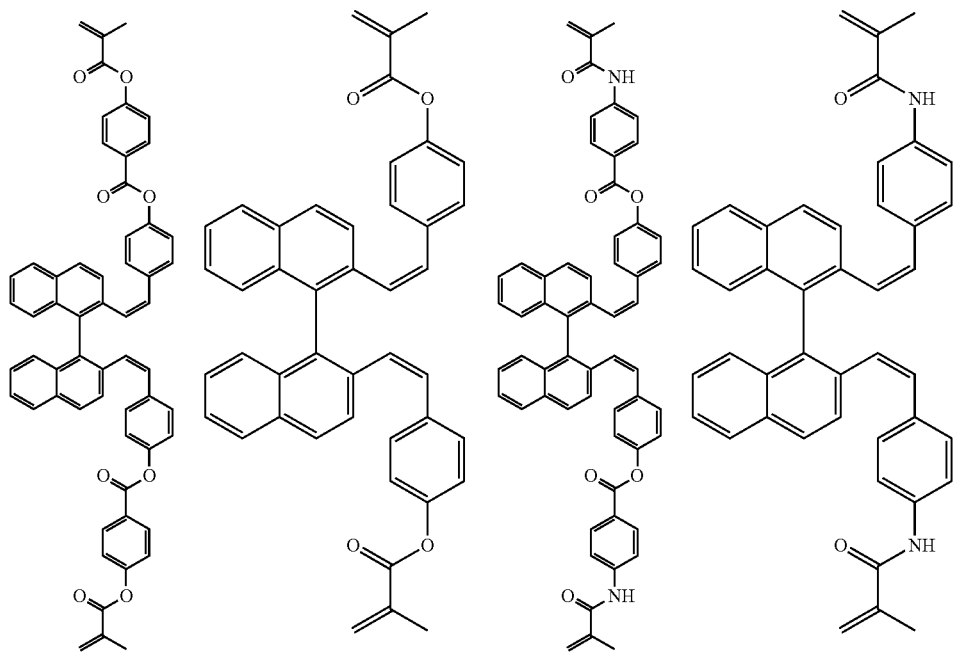
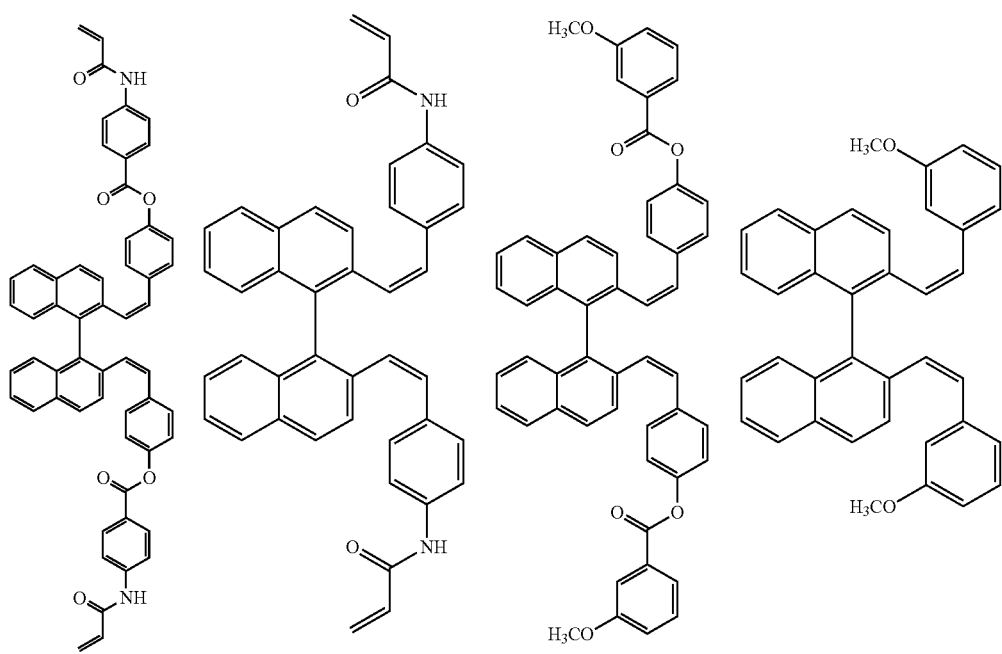

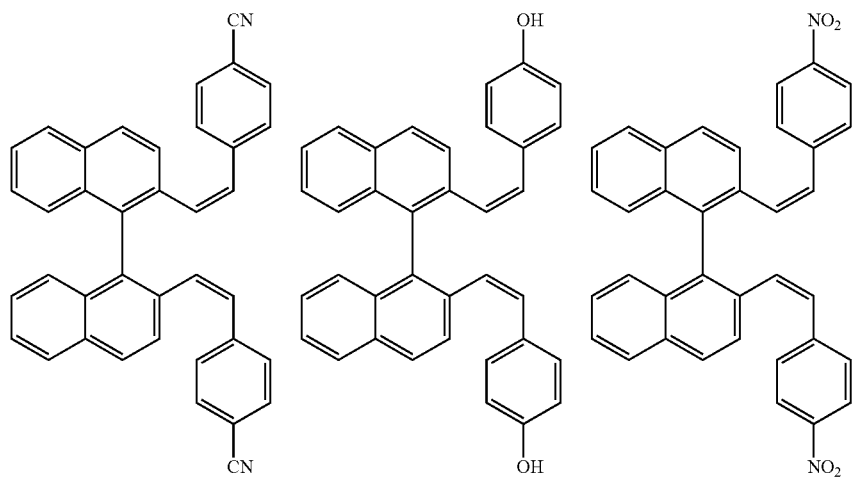
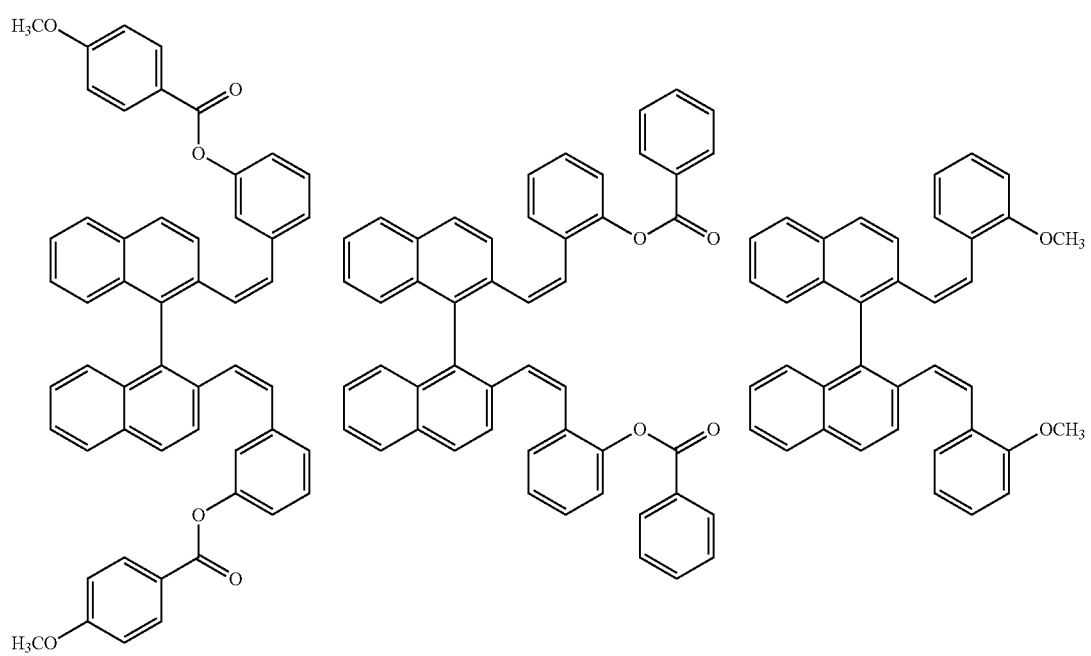

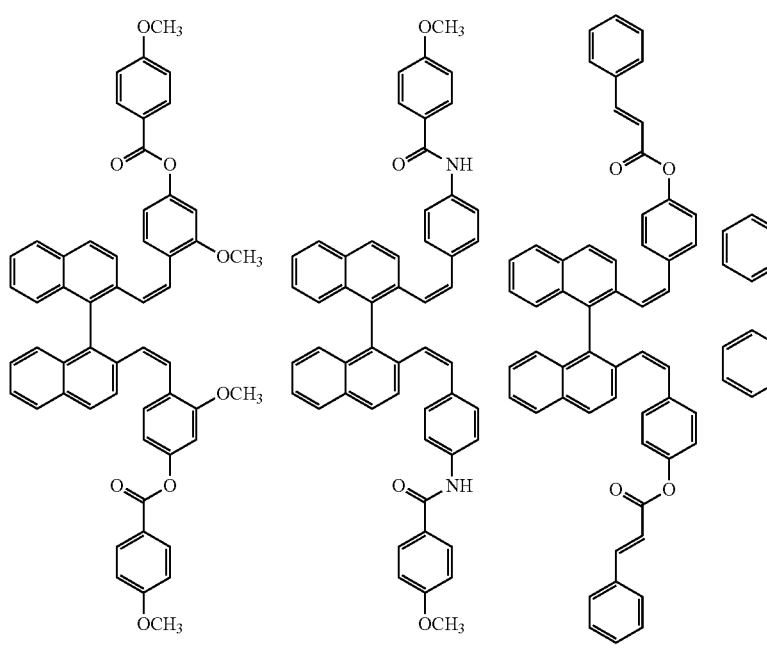
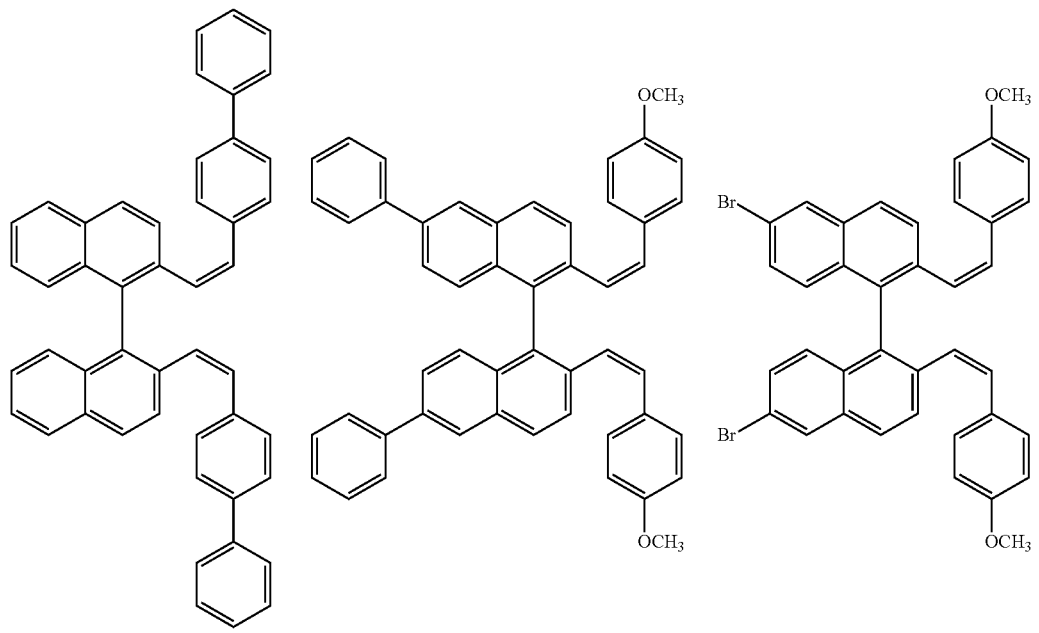

-continued
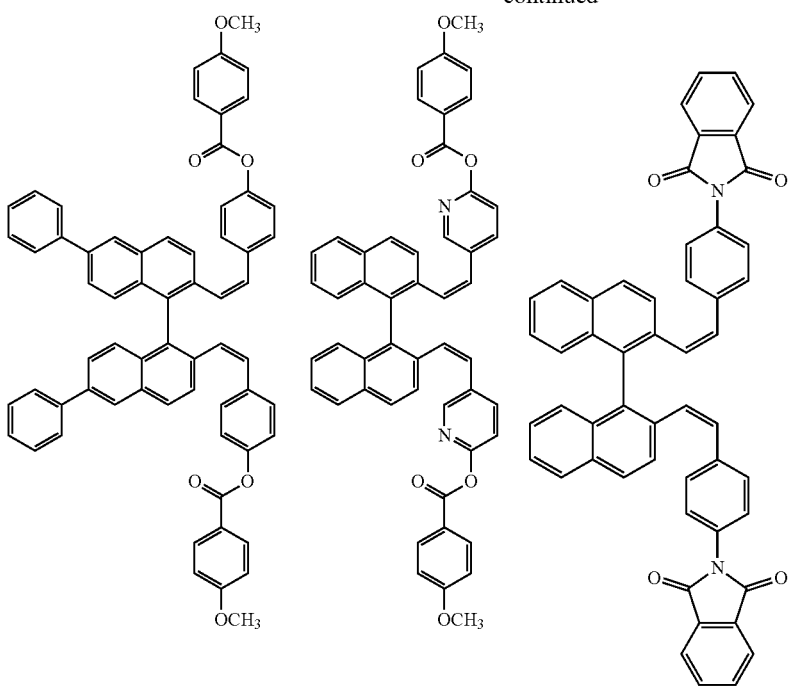
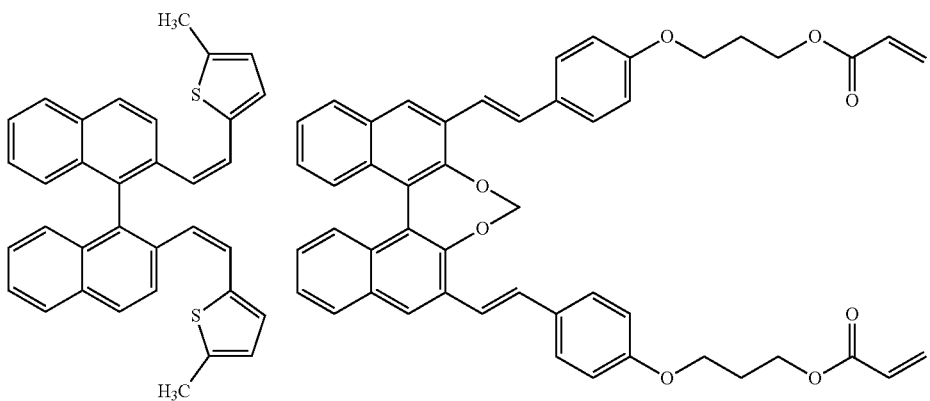
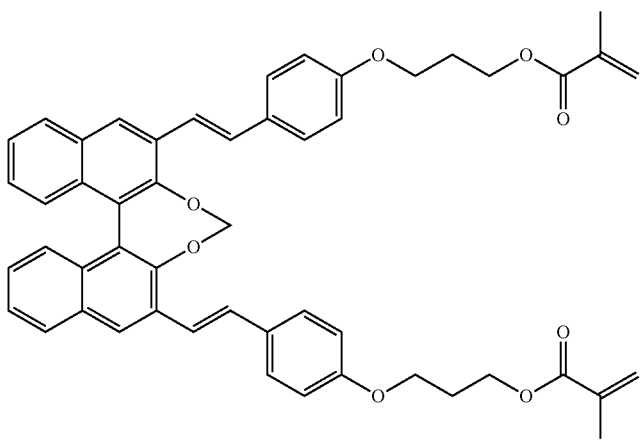

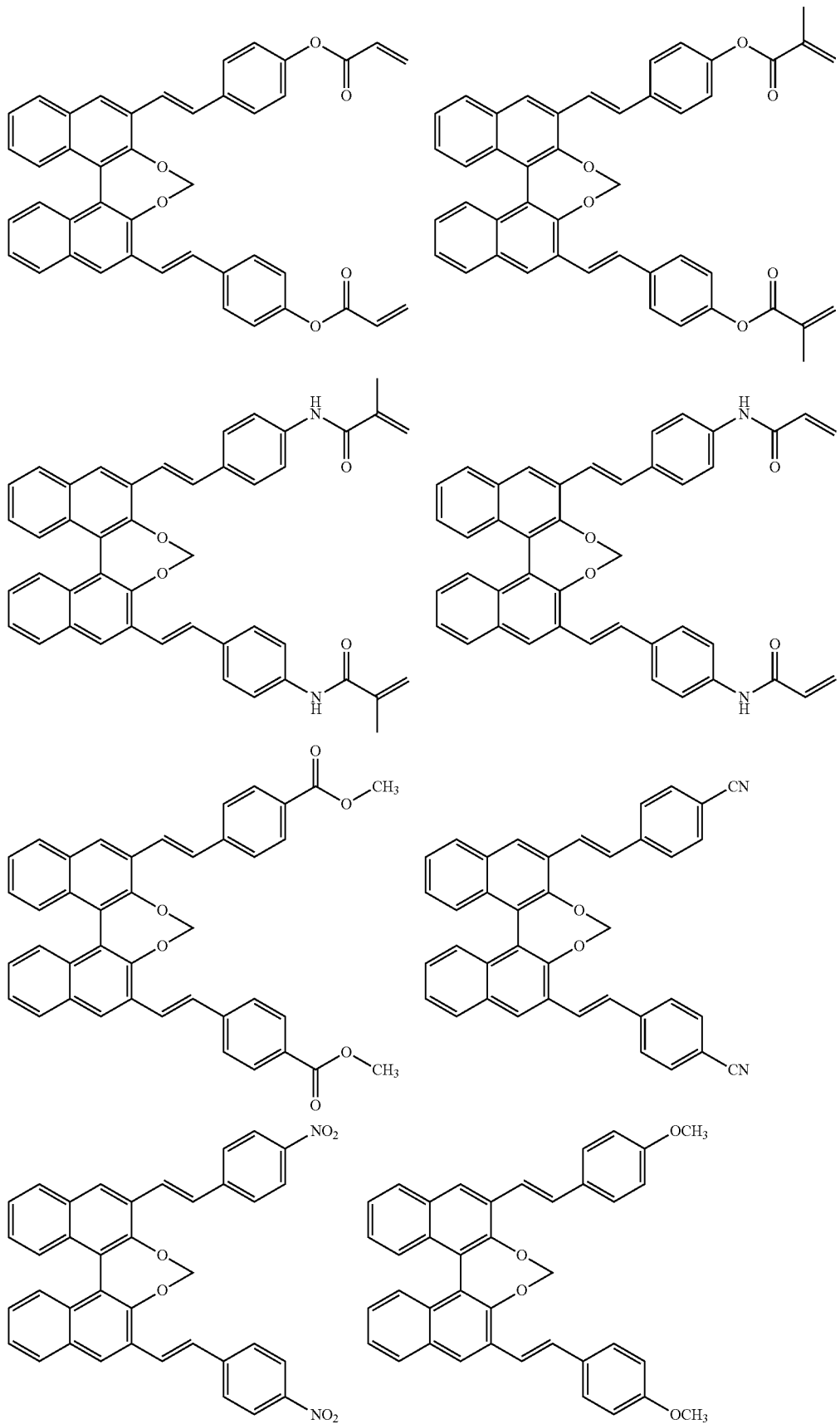

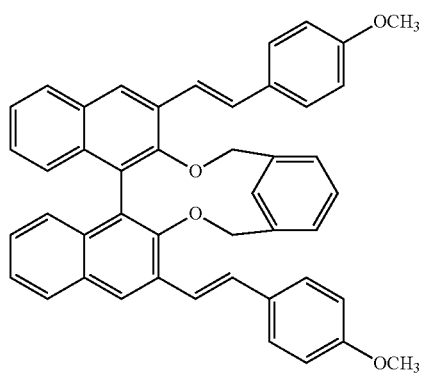
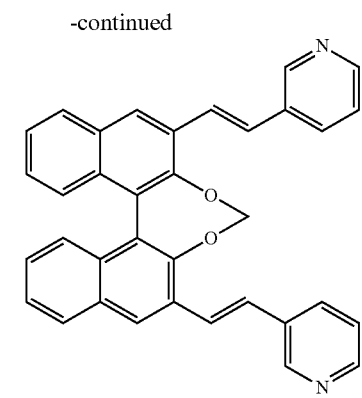
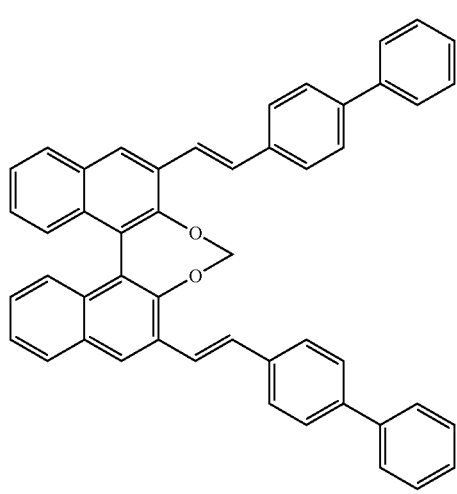
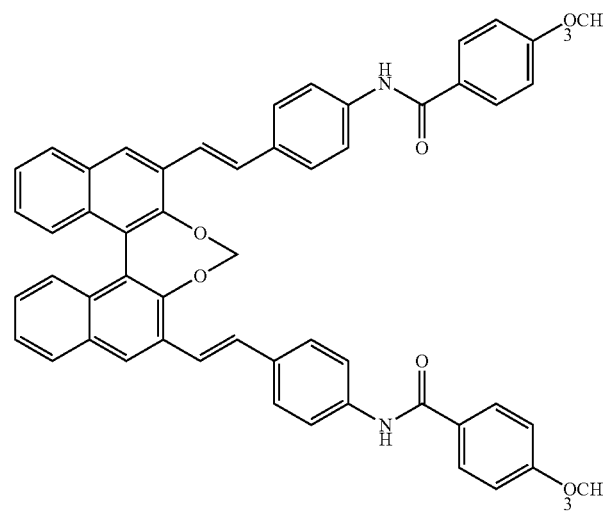
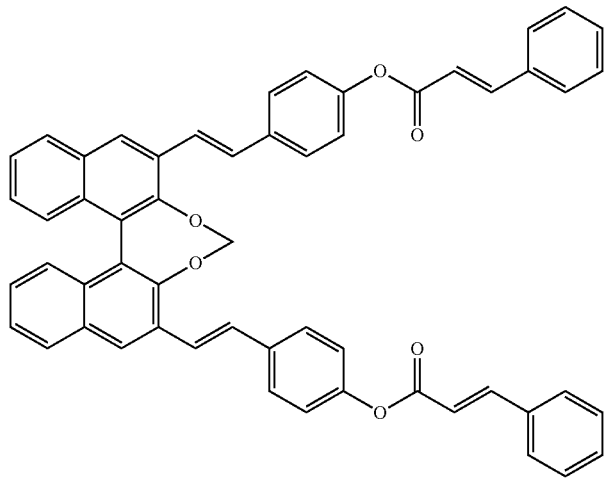

-continued
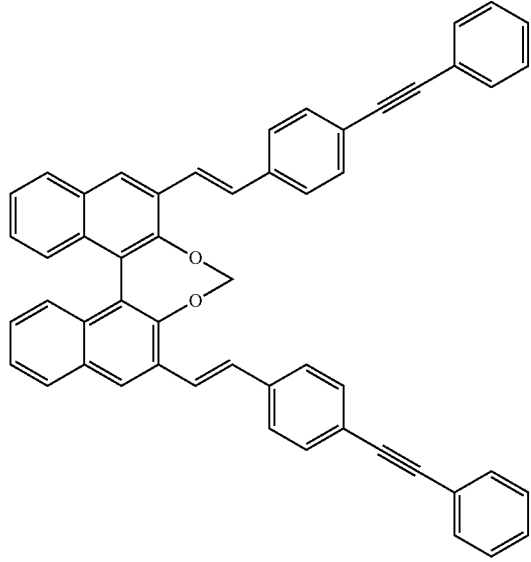
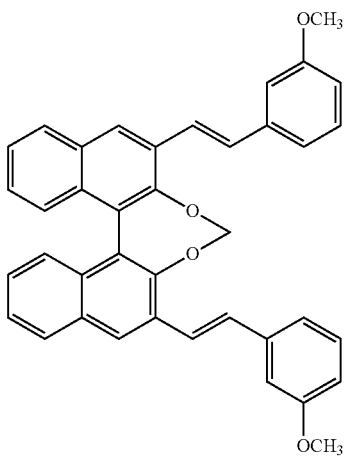
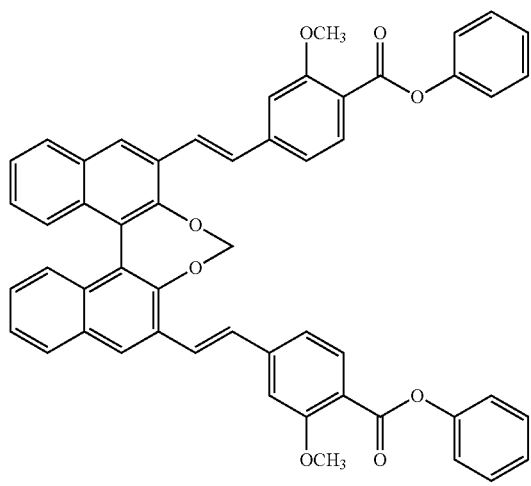
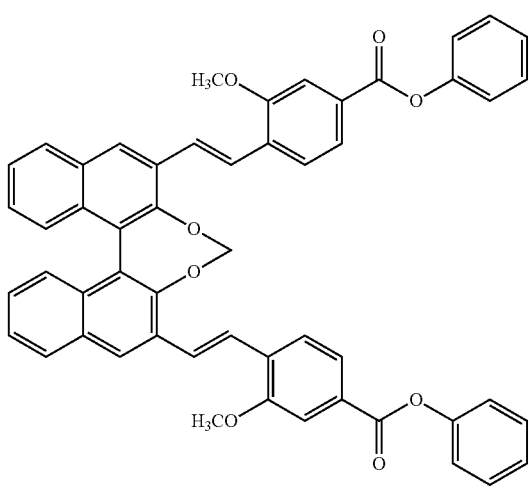
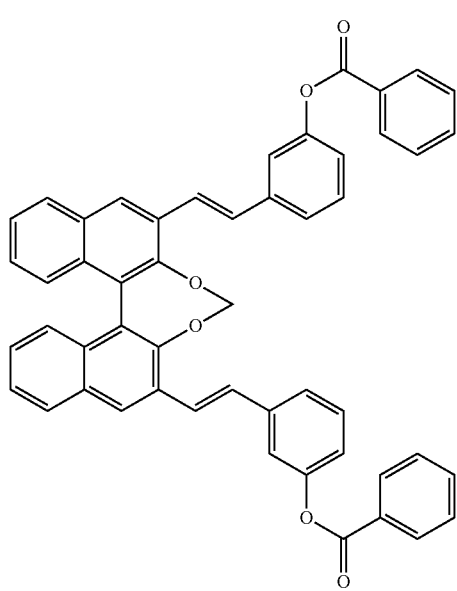
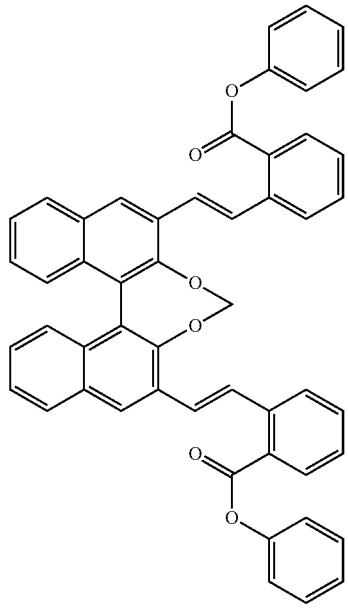

-continued
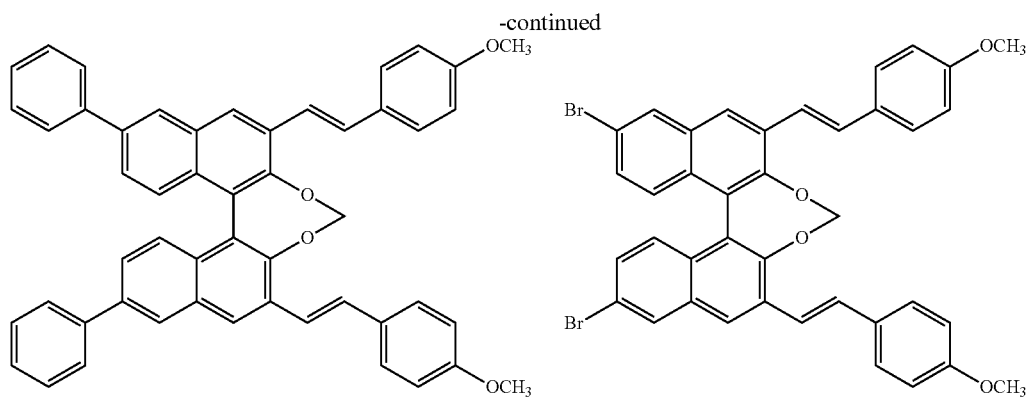
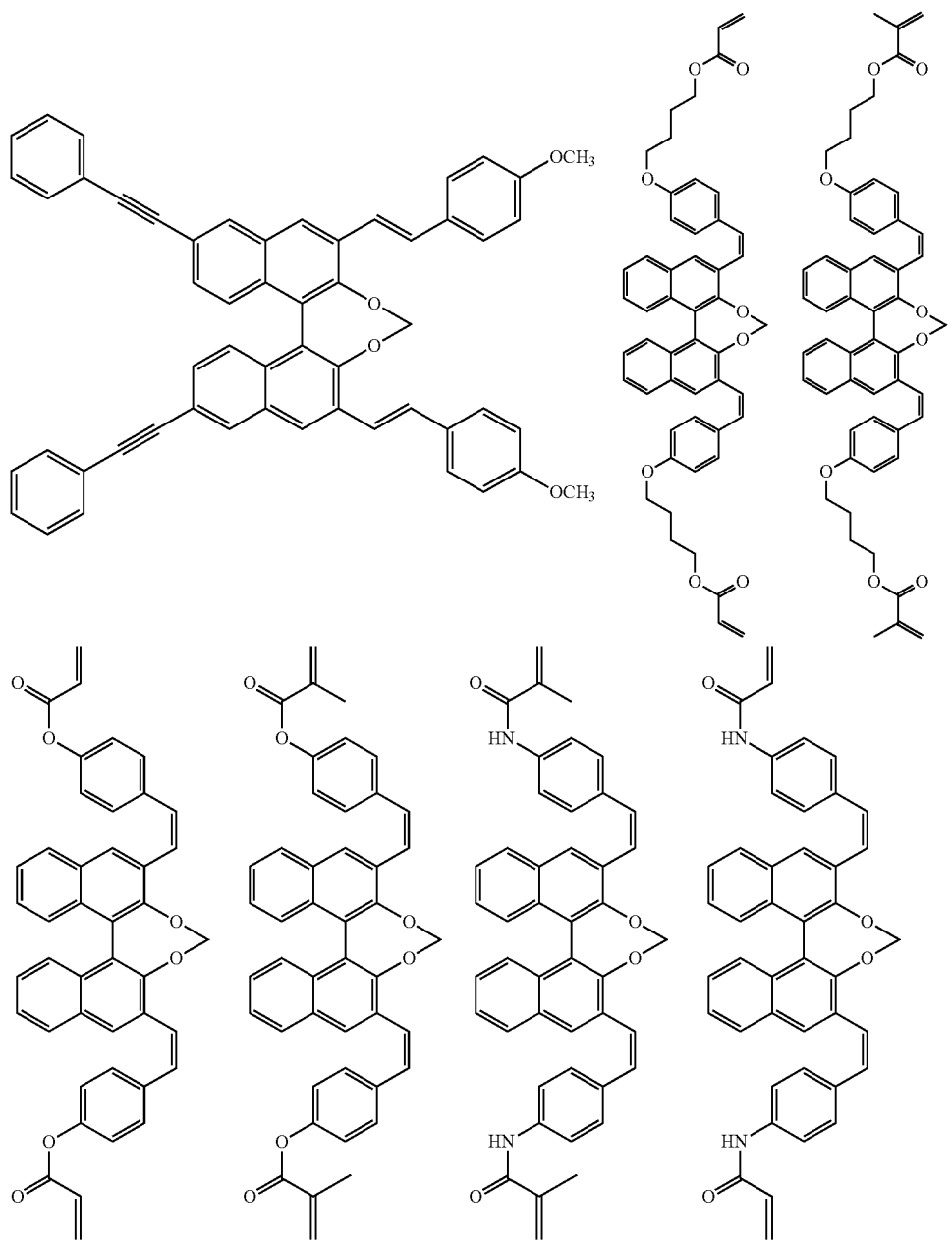

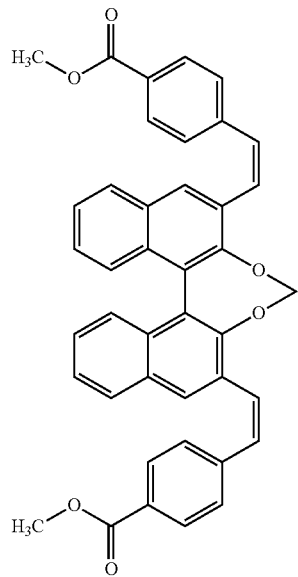
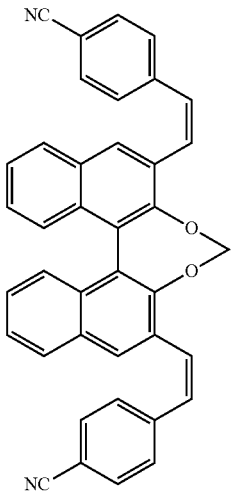
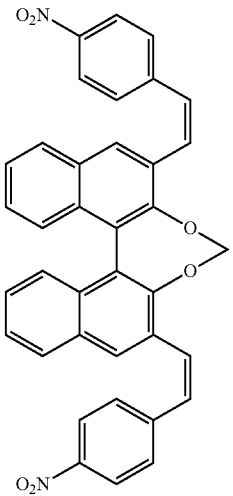
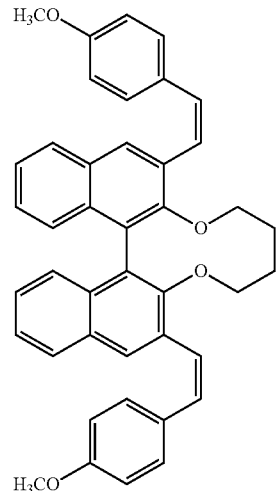
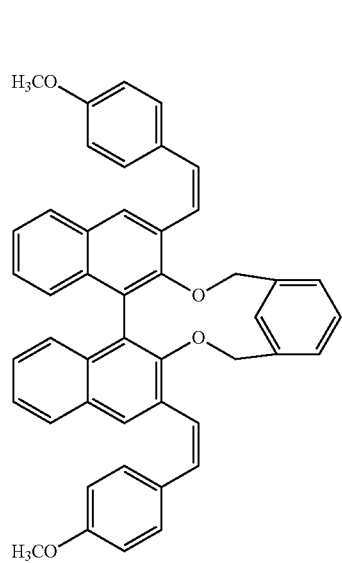
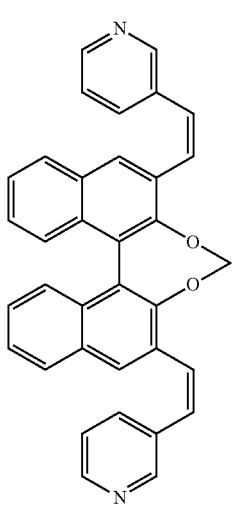
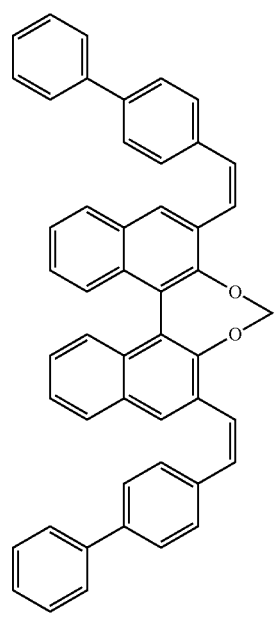

-continued
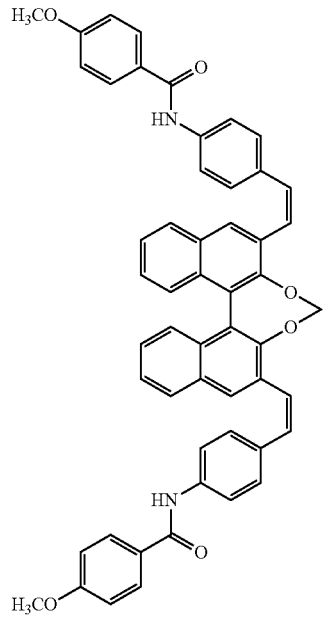
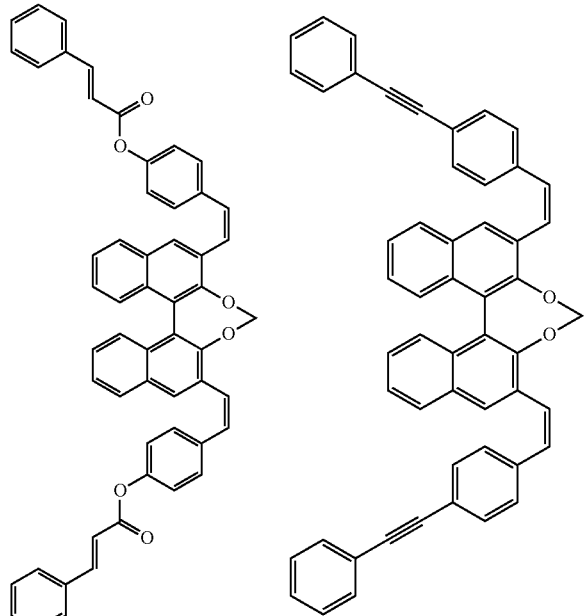
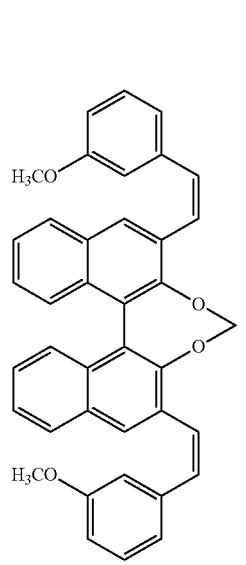
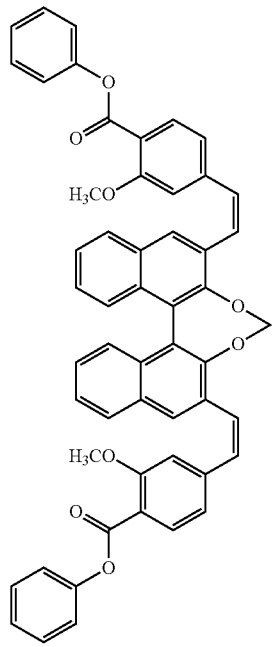
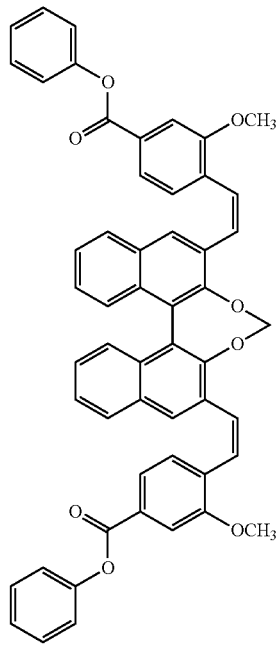

-continued

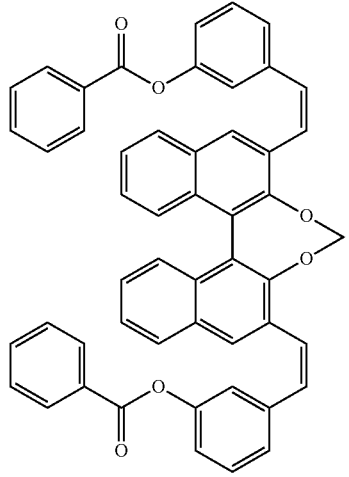
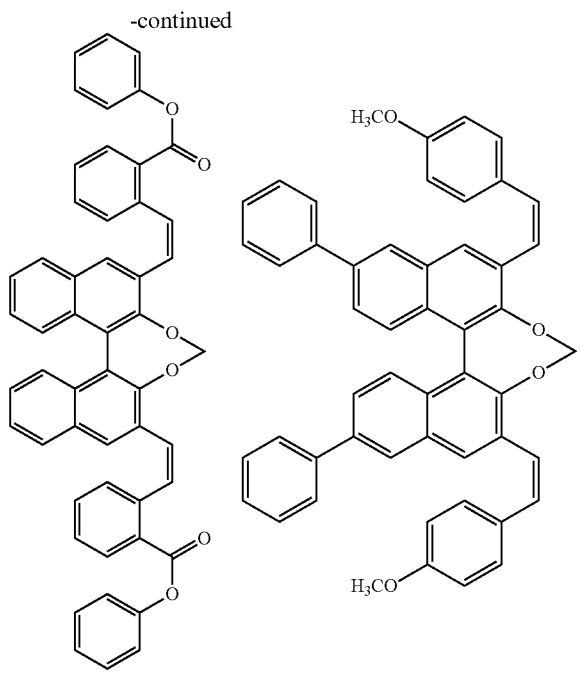

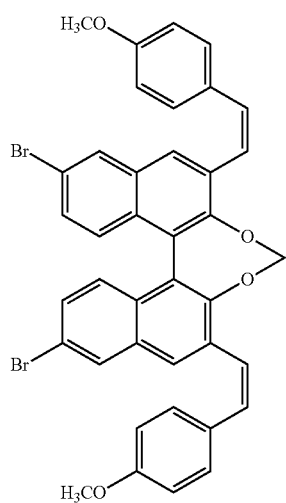
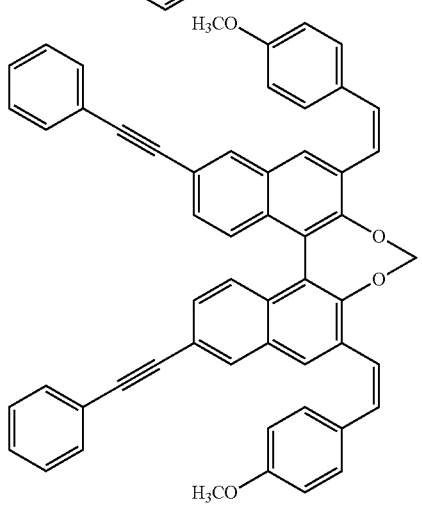

The specific compound can be applied to various uses and is suitably used as a so-called chiral compound. For example, by using a liquid crystal composition obtained by mixing the specific compound and a liquid crystalline compound, a cholesteric liquid crystalline phase can be formed.

Hereinafter, the liquid crystal composition will be described in detail.

[Liquid Crystal Composition]

Next, the liquid crystal composition according to the embodiment of the present invention (hereinafter, also simply referred to as a "specific liquid crystal composition") will be described.

The specific liquid crystal composition includes a specific compound and a liquid crystalline compound.

Hereinafter, various components essential or optionally contained in the specific liquid crystal composition will be described.

[Specific Compound]

The specific liquid crystal composition includes a specific compound. The specific compound is as described above.

The content of the specific compound in the specific liquid crystal composition is not particularly limited, but is preferably 1% to 20% by mass, more preferably 2% to 15% by mass, and still more preferably 2% to 10% by mass with respect to the total mass of the liquid crystalline compound in the composition.

In the specific liquid crystal composition, the specific compound may be used alone or in combination of two or more kinds thereof. In a case where two or more kinds thereof are used, it is preferable that the total content thereof is within the above-described range.

[Liquid Crystalline Compound]

The specific liquid crystal composition includes a liquid crystalline compound. The liquid crystalline compound is a compound other than the specific compound, and means a compound exhibiting liquid crystallinity.

In addition, the "compound exhibiting liquid crystallinity" is intended that the compound has properties of expressing a mesophase between a crystalline phase (low temperature side) and an isotropic phase (high temperature side) in a case of changing a temperature. As a specific observation method, optical anisotropy and fluidity derived from a liquid crystalline phase can be confirmed by performing an observation using a polarizing microscope while heating the compound or lowering a temperature of the compound with a hot stage system FP90, manufactured by METTLER TOLEDO, or the like.

The liquid crystalline compound is not particularly limited as long as it has liquid crystallinity, and examples thereof include a rod-like nematic liquid crystalline compound.

Examples of the rod-like nematic liquid crystalline compound include azomethines, azoxys, cyanobiphenyls, cyanophenyl esters, benzoic acid esters, cyclohexanecarboxylic acid phenyl esters, cyanophenylcyclohexanes, cyano-substituted phenylpyrimidines, alkoxy-substituted phenylpyrimidines, phenyldioxanes, tolans, and alkenylcyclohexylbenzonitriles. High-molecular-weight liquid crystalline compounds can also be used as well as low-molecular-weight liquid crystalline compounds.

The liquid crystalline compound may be polymerizable or non-polymerizable, but is preferably polymerizable.

From the viewpoint that the cholesteric liquid crystalline phase can be immobilized, as the liquid crystalline compound, a liquid crystalline compound having one or more polymerizable groups is preferable, a liquid crystalline compound having two or more polymerizable groups is more preferable, and a liquid crystalline compound having two polymerizable groups is still more preferable.

Rod-like liquid crystalline compounds having no polymerizable group are described in various documents (for example, Y. Goto et al., Mol. Cryst. Liq. Cryst. 1995, Vol. 260, pp. 23 to 28).

Meanwhile, a polymerizable rod-like liquid crystalline compound is obtained by introducing a polymerizable group into the rod-like liquid crystalline compound. Examples of the polymerizable group include an unsaturated polymerizable group, an epoxy group, and an aziridinyl group. Among these, an unsaturated polymerizable group is preferable and an ethylenically unsaturated polymerizable group is more preferable. The polymerizable group can be introduced into the molecule of the rod-like liquid crystalline compound by various methods. The number of polymerizable groups included in the polymerizable rod-like liquid crystalline compound is preferably 1 to 6, more preferably 1 to 3, and still more preferably 2. Two or more kinds of polymerizable rod-like liquid crystalline compounds may be used in combination. In a case of using two or more kinds of polymerizable rod-like liquid crystalline compounds in combination, the alignment temperature can be lowered.

As the liquid crystalline compound, a compound represented by General Formula (LC) is preferable.

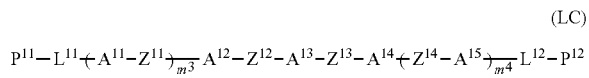
(LC)

In General Formula (LC), $P^{11}$ and $P^{12}$ each independently represent a hydrogen atom or a polymerizable group. However, at least one of $P^{11}$ or $P^{12}$ represents a polymerizable group. $L^{11}$ and $L^{12}$ each independently represent a single bond or a divalent linking group. $A^{11}$ to $A^{15}$ each independently represent an aromatic hydrocarbon ring group or aromatic heterocyclic group which may have a substituent. $Z^{11}$ to $Z^{14}$ each independently represent a single bond or a divalent linking group, $m^3$ and $m^4$ each independently represent an integer of 0 or 1.

In General Formula (LC), the polymerizable group represented by $P^{11}$ and $P^{12}$ is not particularly limited, and suitable specific examples thereof include the polymerizable group represented by General Formulae (P-1) to (P-20) described above. In a case where the polymerizable group represented $P^{11}$ and $P^{12}$ represents General Formulae (P-1) to (P-20) described above, * in General Formulae (P-1) to (P-20) represents a bonding position to $L^{11}$ or $L^{12}$.

It is preferable that at least any one of $P^{11}$ or $P^{12}$ represents a polymerizable group, and it is more preferable that both $P^{11}$ and $P^{12}$ represent a polymerizable group.

In General Formula (LC), the divalent linking group represented by $L^{11}$ and $L^{12}$ is not particularly limited, and examples thereof include a linear or branched alkylene group having 1 to 20 carbon atoms, and a linking group selected from the group consisting of a linear or branched alkylene group having 1 to 20 carbon atoms, in which one or two or more —CH$_2$— is replaced with —O—, —S—, —NH—, —N(CH$_3$)—, —CO—, or —COO—. As the divalent linking group represented by $L^{11}$ and $L^{12}$, a group of a linear or branched alkylene group having 1 to 20 carbon atoms, in which one or two or more —CH$_2$— is replaced with —O— is preferable.

In General Formula (LC), $A^{11}$ to $A^{15}$ each independently represent an aromatic hydrocarbon ring group or aromatic heterocyclic group which may have a substituent.

The number of ring members in the above-described aromatic hydrocarbon ring group is not particularly limited, but is, for example, 5 to 10.

The aromatic hydrocarbon ring constituting the aromatic hydrocarbon ring group may have a monocyclic structure or a polycyclic structure.

The number of carbon atoms in the above-described aromatic hydrocarbon ring is not particularly limited, but is preferably 6 to 18 and more preferably 6 to 10. Specific examples of the aromatic hydrocarbon ring include a benzene ring, a biphenyl ring, a naphthalene ring, an anthracene ring, a phenanthrene ring, and a fluorene ring. Among these, a benzene ring is preferable. The above-described aromatic hydrocarbon ring constitutes an aromatic hydrocarbon ring group by removing two hydrogen atoms on the ring.

The number of ring members in the above-described aromatic heterocyclic group is, for example, 5 to 10.

The aromatic hetero ring constituting the aromatic heterocyclic group may have a monocyclic structure or a polycyclic structure.

Examples of a hetero atom included in the above-described aromatic heterocyclic group include a nitrogen atom, an oxygen atom, and a sulfur atom. The number of carbon atoms in the above-described aromatic hetero ring is not particularly limited, but is preferably 5 to 10. Specific examples of the above-described aromatic hetero ring include a pyridine ring, a pyridazine ring, a pyrimidine ring, a pyrazine ring, a triazine ring, a thiophene ring, a thiazole ring, and an imidazole ring. The above-described aromatic hetero ring constitutes an aromatic heterocyclic group by removing two hydrogen atoms on the ring.

The aromatic hydrocarbon ring group and aromatic heterocyclic group may have a substituent. The type of the substituent is not particularly limited, and examples thereof include known substituents. Examples thereof include a halogen atom, an alkyl group, an alkoxy group, an aryl group, a hydroxyl group, an amino group, a carboxyl group, a sulfonamide group, an N-sulfonylamide group, an acyl group, an acyloxy group, a cyano group, a nitro group, and an alkoxycarbonyl group. Each of the above-described groups may be further substituted with a substituent. For example, a hydrogen atom in the alkyl group may be replaced with a fluorine atom. In addition, the number of substituents is not particularly limited, and the aromatic hydrocarbon ring group and aromatic heterocyclic group may have one substituent or may have a plurality of substituents.

Among these, as the substituent, from the viewpoint that solubility of the compound represented by General Formula (LC) is further improved, a fluorine atom, a chlorine atom, a fluoroalkyl group, an alkoxy group, or an alkyl group is preferable, and a fluoroalkyl group, an alkoxy group, or an alkyl group is more preferable.

The number of carbon atoms in the fluoroalkyl group and alkyl group, and the number of carbon atoms in an alkyl group of the alkoxy group are not particularly limited, but are preferably 1 to 10, more preferably 1 to 5, still more preferably 1 to 3, and particularly preferably 1.

The fluoroalkyl group is a group in which at least one hydrogen atom in the alkyl group is replaced with a fluorine atom, and it is preferable that all hydrogen atoms are replaced with fluorine atoms (so-called perfluoroalkyl group is preferable).

As $A^{11}$ to $A^{15}$, an aromatic hydrocarbon ring group which may have a substituent is preferable, and a phenylene group bonded at the 1-position and the 4-position is more preferable.

In General Formula (LC), the divalent linking group represented by $Z^{11}$ to $Z^{14}$ is not particularly limited, and examples thereof include a divalent aliphatic hydrocarbon group (which may be linear, branched, or cyclic; a divalent aliphatic hydrocarbon group having 1 to 20 carbon atoms is preferable, and examples thereof include an alkylene group; in addition, an alkenylene group or an alkynylene group may be used), —O—, —S—, —SO$_2$—, —NR$^1$—, —CO—, —N=N—, —CH=N—, and a group of a combination of two or more these groups (examples of the group of a combination of two or more groups include —CO—NH—, —CO—S—, and —COO—). Here, R$^1$ represents a hydrogen atom or an alkyl group (preferably having 1 to 10 carbon atoms). A hydrogen atom in the above-described divalent linking group may be replaced with another substituent such as a halogen atom.

As $Z^{11}$ to $Z^{14}$, among these, —COO— or —CH=CH— is preferable.

In General Formula (LC), m$^3$ and m$^4$ each independently represent an integer of 0 or 1, preferably 0.

The compound represented by General Formula (LC) can be synthesized by a known method.

Specific examples of the above-described compound represented by General Formula (LC) are described below, but the compound is not limited thereto.

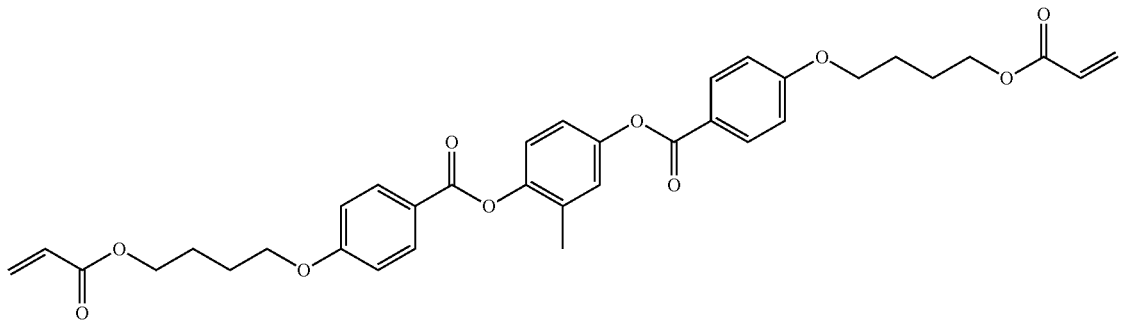

LC-1

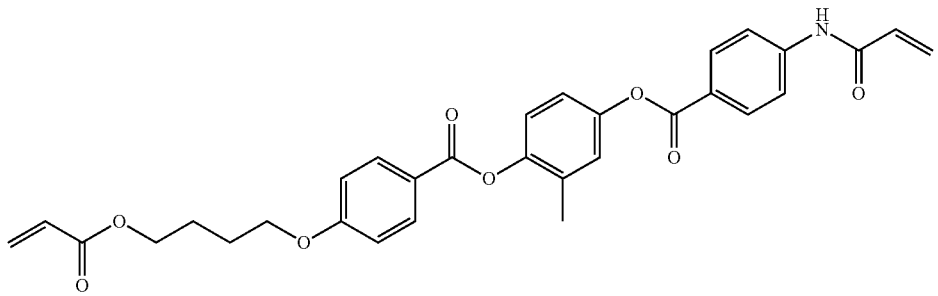

LC-2

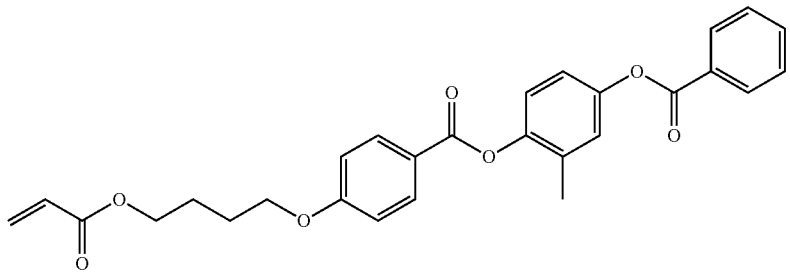

LC-3

-continued
LC-4
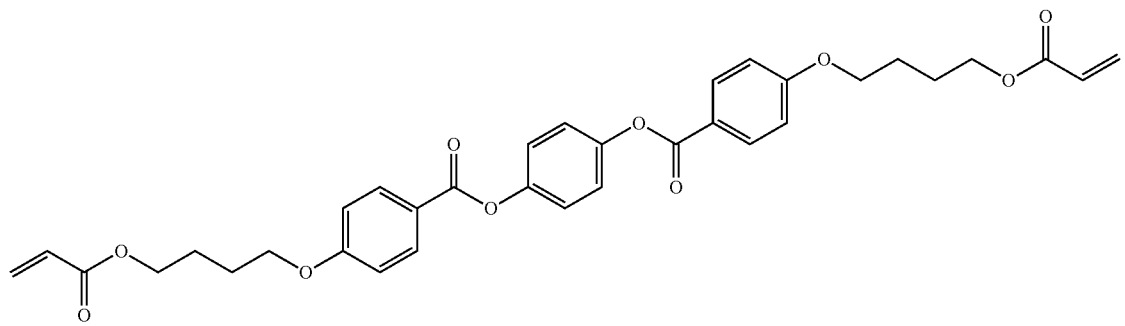
LC-5
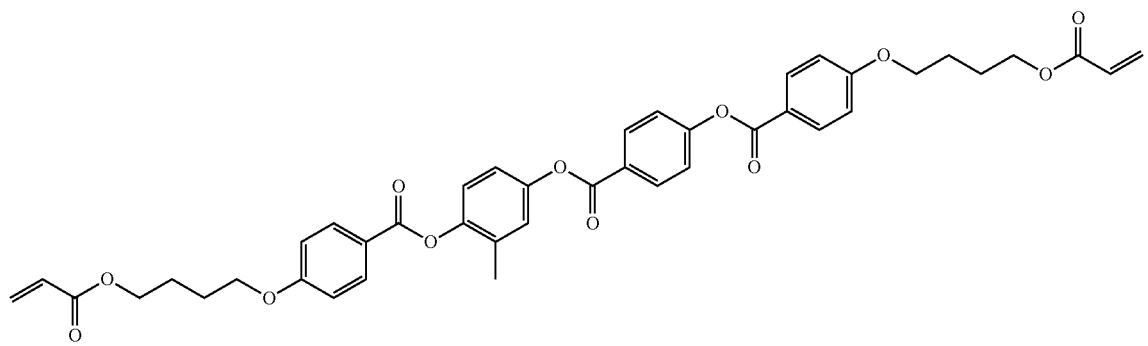
LC-6
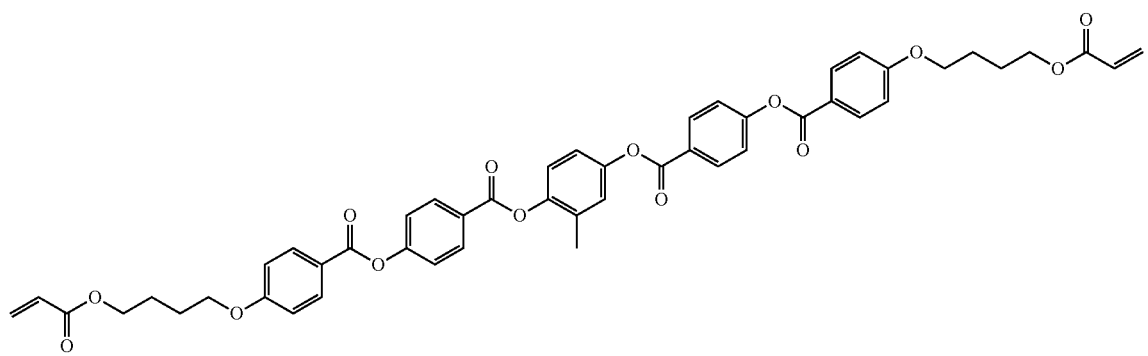
LC-7
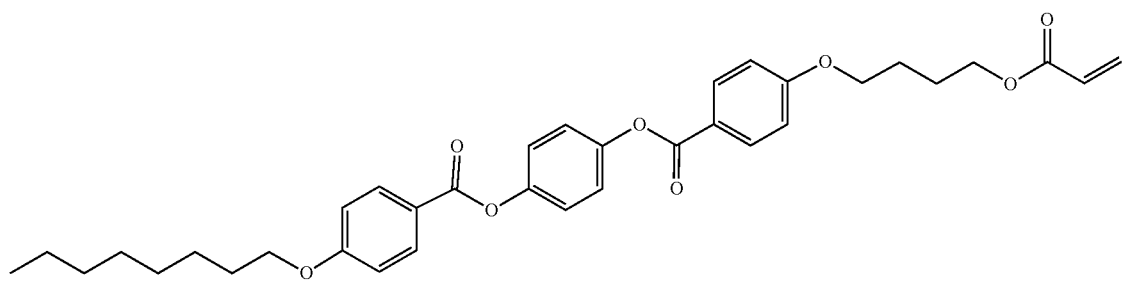

-continued

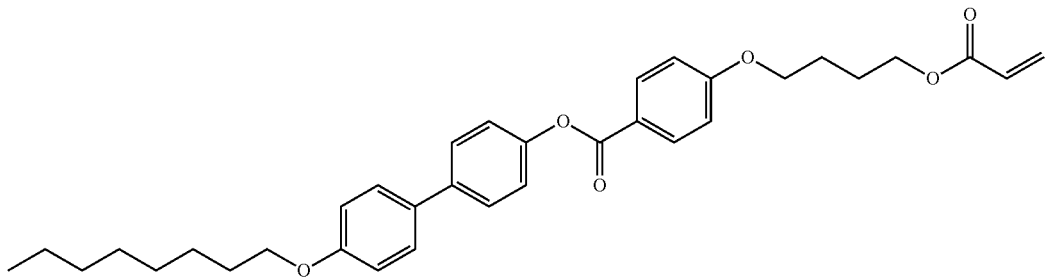
LC-8

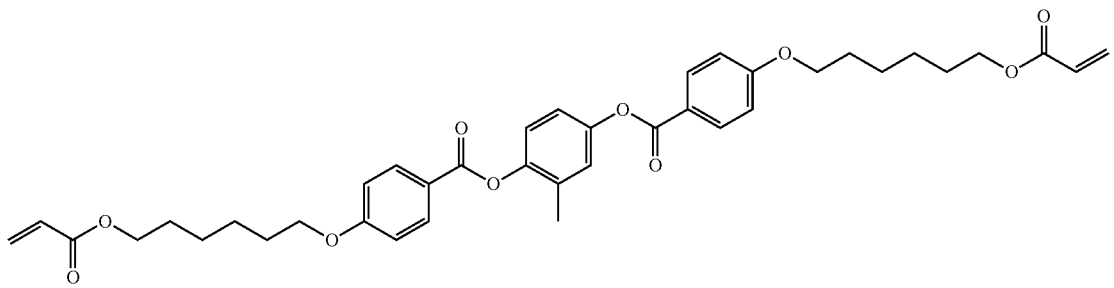
LC-9

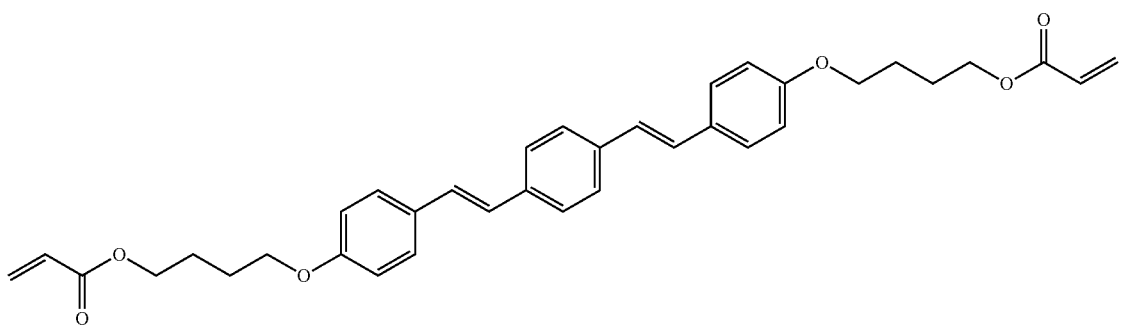
LC-10

The compound represented by General Formula (LC) may be used alone or in combination of a plurality thereof.

The content of the liquid crystalline compound in the specific liquid crystal composition is preferably 5% to 99% by mass, more preferably 25% to 98% by mass, and still more preferably 75% to 98% by mass with respect to the total mass of the composition.

In the specific liquid crystal composition, the liquid crystalline compound may be used alone or in combination of two or more kinds thereof. In a case where two or more kinds thereof are used, it is preferable that the total content thereof is within the above-described range.

[Polymerization Initiator]

The specific liquid crystal composition may include a polymerization initiator.

Examples of the polymerization initiator include a photopolymerization initiator and a thermal polymerization initiator. Among these, a photopolymerization initiator capable of initiating a polymerization reaction by ultraviolet irradiation is preferable. Examples of the photopolymerization initiator include an alkylphenone compound, an α-carbonyl compound, acyloin ether, an α-hydrocarbon-substituted aromatic acyloin compound, a polynuclear quinone compound, a phenazine compound, and an oxadiazole compound. As the alkylphenone compound, for example, IRGACURE 907 or the like is used.

In a case where the specific liquid crystal composition includes a polymerization initiator, the content of the polymerization initiator in the composition is not particularly limited, but is preferably 0.1% to 20% by mass and more preferably 1% to 8% by mass with respect to the total mass of the liquid crystalline compound.

In the specific liquid crystal composition, the polymerization initiator may be used alone or in combination of two or more kinds thereof. In a case where two or more kinds thereof are used, it is preferable that the total content thereof is within the above-described range.

[Surfactant]

The specific liquid crystal composition may include a surfactant which contributes to a stable or rapid formation of liquid crystalline phase (for example, a nematic phase and a cholesteric phase).

Examples of the surfactant include a fluorine-containing (meth)acrylate-based polymer, compounds represented by General Formulae (X1) to (X3) described in WO2011/162291A, compounds represented by General Formula (I) described in paragraphs 0082 to 0090 of JP2014-119605A, and compounds described in paragraphs 0020 to 0031 of JP2013-47204A (JP5774518B). At an air interface of a layer, these compounds can reduce a tilt angle of molecules of a liquid crystalline compound or can cause a liquid crystalline compound to be substantially horizontally aligned.

In the present specification, "horizontally aligned" means that a molecular axis of the liquid crystalline compound (which corresponds to a major axis of the liquid crystalline compound in a case where the liquid crystalline compound is a rod-like liquid crystalline compound) is parallel to a surface of the layer of the composition (film surface), but the molecular axis is not required to be strictly parallel thereto. In the present specification, the "horizontally aligned" means an alignment in which a tilt angle with the film surface is less than 20 degrees. In a case where the liquid crystalline compound is horizontally aligned near the air interface, alignment defects are less likely to occur, so that transparency in a visible light region is increased. On the other hand, in a case where the molecules of the liquid crystalline compound are aligned at a large tilt angle with respect to the film surface, for example, in a case of cholesteric phase, since a helical axis thereof deviates from a normal line of the film surface, reflectivity may decrease, fingerprint patterns may occur, or haze may increase or diffractivity may be exhibited, which are not preferable.

Examples of the fluorine-containing (meth) acrylate-based polymer which can be used as the surfactant also include polymers described in paragraphs 0018 to 0043 of JP2007-272185A.

In a case where the specific liquid crystal composition includes a surfactant, the content of the surfactant is not particularly limited, but is preferably 0.001% to 10% by mass and more preferably 0.05% to 3% by mass with respect to the total mass of the liquid crystalline compound.

In the specific liquid crystal composition, the surfactant may be used alone or in combination of two or more kinds thereof. In a case where two or more kinds thereof are used, it is preferable that the total content thereof is within the above-described range.

[Solvent]

The specific liquid crystal composition may include a solvent. As the solvent, a solvent which can dissolve each component of the composition is preferable. Examples thereof include methyl ethyl ketone, cyclohexanone, and a mixed solvent thereof.

In a case where the specific liquid crystal composition includes a solvent, the content of the solvent in the specific liquid crystal composition is preferably an amount at which the concentration of solid contents of the composition is 5% to 50% by mass, and more preferably an amount at which the concentration of solid contents in the composition is 10% to 40% by mass.

The solid contents mean components other than a solvent in the composition. In a case where a component is not a solvent, the component is regarded as a solid content even in a case where the property of the component is liquid.

In the specific liquid crystal composition, the solvent may be used alone or in combination of two or more kinds thereof. In a case where two or more kinds thereof are used, it is preferable that the total content thereof is within the above-described range.

In addition to the above-described components, the specific liquid crystal composition may also include other additives such as an antioxidant, an ultraviolet absorber, a sensitizer, a stabilizer, a plasticizer, a chain transfer agent, a polymerization inhibitor, an anti-foaming agent, a leveling agent, a thickener, a flame retardant, a dispersant, a polymerizable monomer, and a coloring material such as a dye and a pigment.

[Cured Product]

The present invention also includes a cured product obtained by curing the specific liquid crystal composition.

[Curing Method and Cured Product]

A method for curing (polymerizing and curing) the specific liquid crystal composition is not particularly limited, and a known method can be adopted. Examples thereof include an aspect which includes a step X of bringing a predetermined substrate into contact with the specific liquid crystal composition to form a composition layer on the substrate, a step Y of exposing the composition layer, and a step Z of subjecting the composition layer to a curing treatment.

According to this aspect, the liquid crystalline compound can be immobilized in an aligned state, and a so-called optically anisotropic body or a layer obtained by immobilizing a cholesteric liquid crystalline phase can be formed.

Hereinafter, the procedures of steps X to Z will be described in detail.

The step X is a step of bringing a substrate into contact with the specific liquid crystal composition to form a composition layer on the substrate. The type of the substrate to be used is not particularly limited, and examples thereof include known substrates (for example, a resin substrate, a glass substrate, a ceramic substrate, a semiconductor substrate, and a metal substrate).

A method of bringing the substrate into contact with the specific liquid crystal composition is not particularly limited, and examples thereof include a method of applying the specific liquid crystal composition to the substrate and a method of immersing the substrate in the specific liquid crystal composition.

After bringing the substrate into contact with the specific liquid crystal composition, as necessary, a drying treatment may be performed in order to remove a solvent from the composition layer on the substrate. In addition, a heat treatment may be performed in order to promote the alignment of the liquid crystalline compound to be a liquid crystalline phase.

The step Y is a step of subjecting the composition layer to an exposure treatment using i-rays (wavelength: 365 nm) or the like.

In the specific compound, it is preferable that photoisomerization occurs due to the exposure treatment, so that HTP of the compound changes. In the exposure treatment, the degree of change in HTP can also be adjusted by appropriately adjusting the exposure amount, and/or the exposure wavelength and the like.

After the exposure, a heat treatment may be further performed in order to promote the alignment of the liquid crystalline compound to be a liquid crystalline phase.

The helical pitch (and thus the selective reflection wavelength and the like) of the liquid crystalline phase obtained here reflects HTP adjusted in the above-described exposure treatment.

The step Z is a step of subjecting the composition layer undergone the step Y to a curing treatment.

A method of the curing treatment is not particularly limited, and examples thereof include a photo-curing treatment and a thermal-curing treatment. Among these, a photo-curing treatment is preferable.

In a case where a photo-curing treatment is performed as the curing treatment, it is preferable that the specific liquid crystal composition includes a photopolymerization initiator. The wavelength of the light irradiated in the photo-curing treatment is preferably different from the wavelength of the light used in the above-described exposure treatment, or it is preferable that the photopolymerization initiator is not sensitive to the wavelength of the light used in the exposure treatment.

By the above-described curing treatment, a layer obtained by immobilizing the cholesteric liquid crystalline phase is formed. The layer obtained by immobilizing the cholesteric liquid crystalline phase no longer needs to exhibit liquid crystallinity anymore. More specifically, for example, as a state in which the cholesteric liquid crystalline phase is "immobilized," the most typical and preferred aspect is a state in which the alignment of the liquid crystalline compound, which is the cholesteric liquid crystalline phase, is retained. More specifically, the state is preferably a state in which the layer does not exhibit fluidity within a temperature range of usually 0° C. to 50° C., and under more severe conditions of a temperature range of −30° C. to 70° C., and in which the immobilized alignment morphology can be kept stable without being changed due to an external field or an external force.

[Optically Anisotropic Body and Reflective Film]

The specific liquid crystal composition can be applied to various uses. For example, the specific liquid crystal composition can be used to form an optically anisotropic body or a reflective film. For example, in a case where the liquid crystalline compound has a polymerizable group, a cured product can be obtained by subjecting the specific liquid crystal composition to a curing treatment (light irradiation treatment, heat treatment, or the like), and the cured product can be suitably applied to an optically anisotropic body or a reflective film.

The optically anisotropic body is intended to be a substance having optical anisotropy.

In addition, the reflective film corresponds to a layer obtained by immobilizing the cholesteric liquid crystalline phase, and can reflect light in a predetermined reflection band.

Examples

Hereinafter, the present invention will be described in more detail based on examples. The materials, the amounts of materials to be used, the proportions, the treatment details, the treatment procedure, or the like shown in the examples below may be modified appropriately as long as the modifications do not depart from the spirit of the present invention. Accordingly, the scope of the present invention should not be construed as being limited to the following examples.

[Synthesis of Compound]

[Synthesis of Compound CD-2]

A compound CD-2 was synthesized according to the following scheme. Me represents a methyl group, and Et represents an ethyl group.

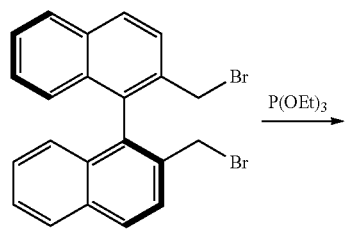

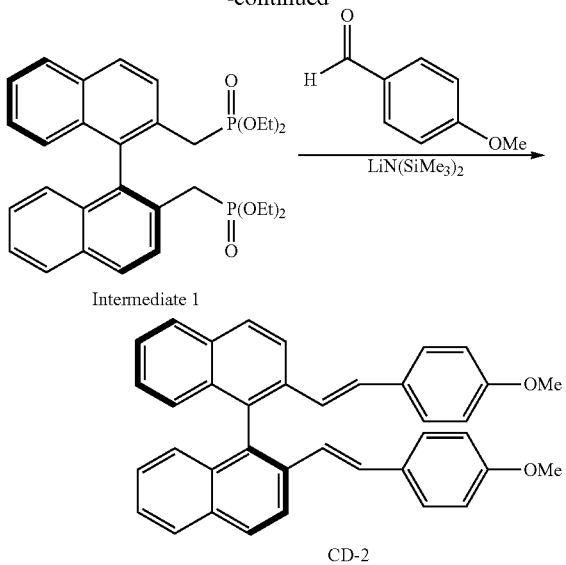

<Synthesis of Intermediate 1>

5.40 g of (S)-2,2'-bis(bromomethyl)-1,1'-binaphthalene (manufactured by Daicel Corporation) and 10.3 mL of P(OEt)$_3$ (manufactured by FUJIFILM Wako Pure Chemical Corporation) were put into a 100 mL eggplant flask. After heating the obtained mixture to 110° C. and stirring for 9 hours, the obtained crude product was purified by silica gel column chromatography using ethyl acetate/methanol (volume ratio: 9:1) as a developing solvent. The solvent was evaporated from the separated solution under reduced pressure, thereby obtaining an intermediate 1 (2.87 g, 42%).

<Synthesis of CD-2>

0.51 g of the above-described intermediate 1, 6 mL of tetrahydrofuran (THF, manufactured by FUJIFILM Wako Pure Chemical Corporation), and 0.56 mL of p-methoxybenzaldehyde (manufactured by FUJIFILM Wako Pure Chemical Corporation) were put into a 100 mL three-neck flask. After cooling the obtained mixture to 0° C., 5.6 mL of a THF solution of 1.3 M lithium bistrimethylsilylamide (manufactured by Tokyo Chemical Industry Co., Ltd.) was added dropwise thereto. After stirring the mixture after dropwise addition at 70° C. for 9 hours, the mixture was cooled to room temperature, and the organic layer was extracted by adding 60 mL of saturated NH$_4$Cl water and 50 mL of ethyl acetate. The solvent was evaporated from the obtained solution under reduced pressure, 20 mL of methanol, 20 mL of ethyl acetate, and 100 mL of saturated sodium bicarbonate water were added to the crude product and stirred for 30 seconds, and then 100 mL of water and 100 mL of ethyl acetate were added thereto to extract the organic layer. The obtained solution was washed twice with saturated saline and dried over magnesium sulfate, and the solvent was evaporated under reduced pressure. The obtained crude product was purified by silica gel column chromatography using ethyl acetate/hexane (volume ratio: 4:6) as a developing solvent. The solvent was evaporated from the separated solution under reduced pressure, thereby obtaining CD-2 (188 mg, yield: 40%).

$^1$H-NMR (300 MHz, DMSO-d$_6$): δ 8.22 (d, 8.7 Hz, 2H), 8.13 (d, 8.7 Hz, 2H), 8.04 (d, 8.1 Hz, 2H), 7.46 (ddd, 8.4 Hz, 8.4 Hz, 1.2 Hz, 2H), 7.35 (d, 16.5 Hz, 2H), 7.26 (ddd, 8.4 Hz, 8.4 Hz, 1.2 Hz, 2H), 7.02 (d, 9.0 Hz, 4H), 6.90 (d, 8.1 Hz, 4H), 6.43 (d, 16.5 Hz, 2H), 3.66 (s, 6H)

[Synthesis of Compound CD-12]

A compound CD-12 was synthesized according to the following scheme.

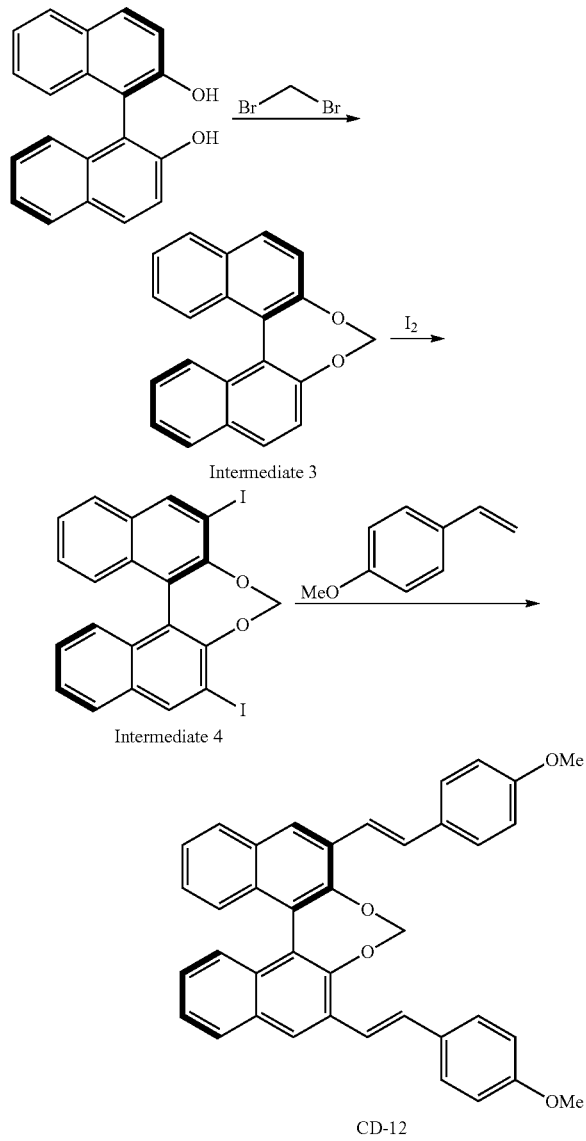

CD-12

<Synthesis of Intermediate 3>

25.00 g of (S)-1,1'-binaphthol (manufactured by KANTO CHEMICAL CO., INC.), 38 mL of butyl acetate (manufactured by FUJIFILM Wako Pure Chemical Corporation), and 38 mL of N,N-dimethylformamide (DMF, manufactured by FUJIFILM Wako Pure Chemical Corporation) were put into a 2 L three-neck flask. After adding 36.27 g of potassium carbonate (manufactured by FUJIFILM Wako Pure Chemical Corporation) to the obtained mixture, 7.9 mL of dibromomethane (FUJIFILM Wako Pure Chemical Corporation) was added dropwise thereto. After stirring the mixture after dropwise addition at 90° C. for 7 hours, the mixture was cooled to room temperature, and the inorganic salt was filtered off. After adding 78 mL of ethyl acetate to the filtrate and increasing the temperature to 45° C., 250 mL of methanol (manufactured by FUJIFILM Wako Pure Chemical Corporation) and 500 mL of water were added thereto, and the mixture was stirred for 30 minutes while cooling with ice. The precipitated solid was filtered to obtain an intermediate 3 (16.6 g, yield: 64%).

<Synthesis of Intermediate 4>

2.84 g of the above-described intermediate 3 and 140 mL of diethyl ether (manufactured FUJIFILM Wako Pure Chemical Corporation) were put into a 500 mL three-neck flask. After adding 5.2 mL of tetramethylethylenediamine (manufactured FUJIFILM Wako Pure Chemical Corporation) to the obtained mixture, 22 mL of a hexane solution of 1.6 M n-butyllithium (manufactured by FUJIFILM Wako Pure Chemical Corporation) was added dropwise thereto, and the mixture was stirred at room temperature for 6 hours to obtain a reaction solution. Next, a solution obtained by dissolving 9.5 g of iodine (manufactured by FUJIFILM Wako Pure Chemical Corporation) in 75 mL of diethyl ether (manufactured by FUJIFILM Wako Pure Chemical Corporation) was added to the above-described reaction solution cooled to −78° C. After heating the obtained reaction solution to room temperature, the reaction solution was stirred for another 10 hours. After stirring, a sodium disulfite aqueous solution (5.7 g of sodium disulfite (manufactured by FUJIFILM Wako Pure Chemical Corporation) and 24 mL of water) and 30 mL of ethyl acetate were added to the above-described reaction solution, and the organic layer was extracted. The obtained solution was washed with saturated saline and dried over magnesium sulfate, and the solvent was evaporated under reduced pressure. The crude product was filtered after reslurry with 10 mL of ethyl acetate (manufactured by FUJIFILM Wako Pure Chemical Corporation) to obtain an intermediate 4 (2.25 g, 43%).

<Synthesis of CD-12>

1.00 g of the above-described intermediate 4, 7.3 mg of p-methoxyphenol (manufactured by FUJIFILM Wako Pure Chemical Corporation), 74.6 mg of triphenylphosphine (manufactured by Tokyo Chemical Industry Co., Ltd.), 6 mL of DMF (manufactured by FUJIFILM Wako Pure Chemical Corporation), and 0.61 mL of p-methoxystyrene were put into a 100 mL three-neck flask. After deoxidizing the inside of the three-neck flask, 2.55 mL of triethylamine (manufactured by FUJIFILM Wako Pure Chemical Corporation) and 41.6 mg of palladium(II) acetate (manufactured by FUJIFILM Wako Pure Chemical Corporation) were added to the mixture in the three-neck flask, and the mixture was stirred at 80° C. for 4 hours. After stirring, the obtained reaction solution was cooled to room temperature, 20 mL of ethyl acetate (manufactured by FUJIFILM Wako Pure Chemical Corporation) was added thereto, the mixture was filtered through Celite, and 30 mL of 0.1 N hydrochloric acid water was added thereto to extract the organic layer. The obtained solution was washed with saturated sodium bicarbonate water and saturated saline, respectively, and dried over magnesium sulfate, and the solvent was evaporated under reduced pressure. The obtained crude product was purified by silica gel column chromatography using ethyl acetate/hexane (volume ratio: 2:8) as a developing solvent. The solvent was evaporated from the separated solution under reduced pressure, thereby obtaining CD-12 (0.302 g, yield: 30%).

[Synthesis of Compounds CD-1, CD-3 to CD-11, and CD-13 to CD-16]

With reference to the above-described method, compounds CD-1, CD-3 to CD-11, and CD-13 to CD-16 were synthesized.

The structures of the compounds CD-1 to CD-16 are shown below.

CD-1
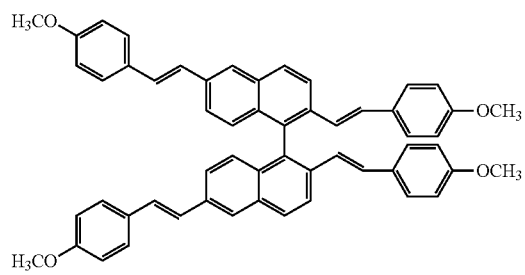
CD-2
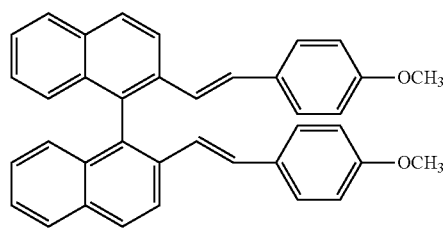
CD-3
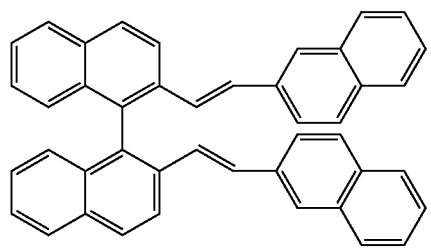
CD-4
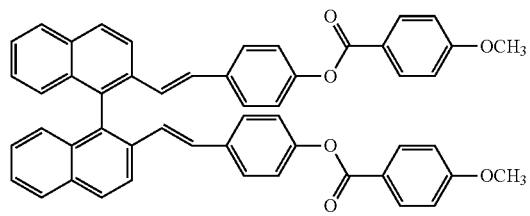
CD-5
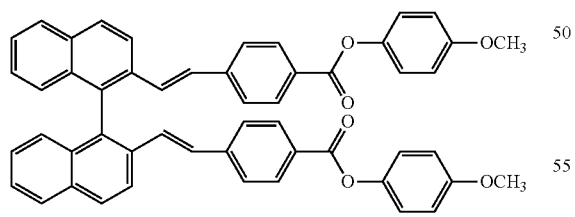
CD-6
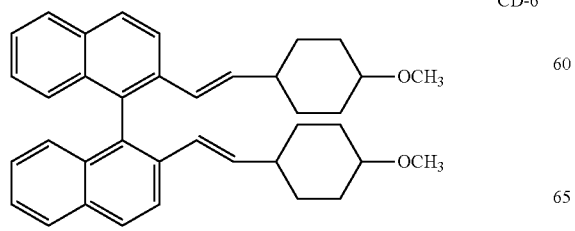
CD-7
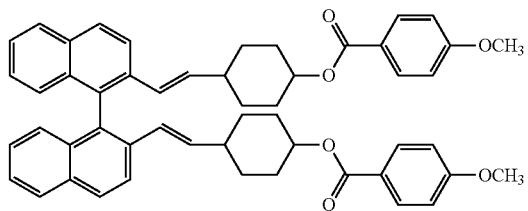
CD-8
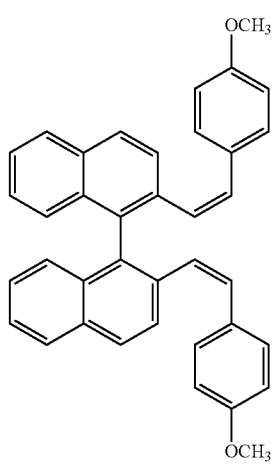
CD-9
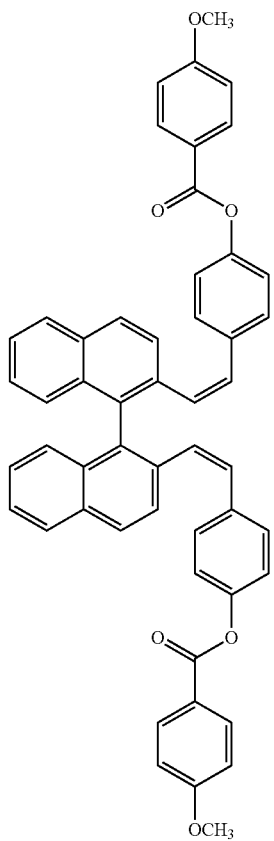

CD-10
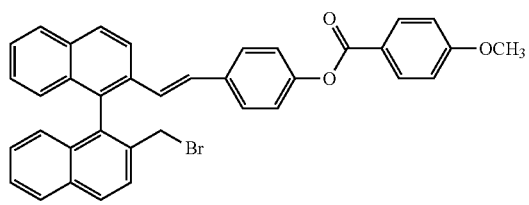

CD-11
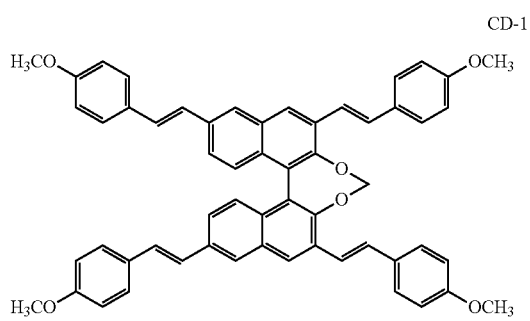

CD-12
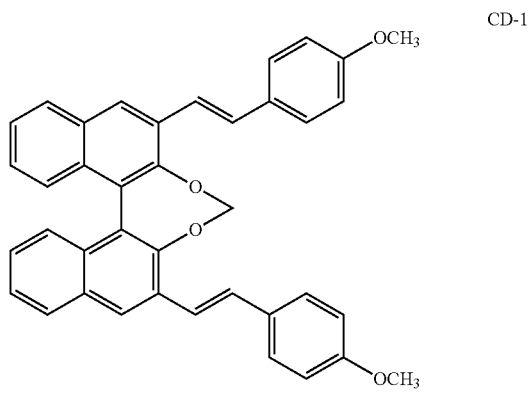

CD-13
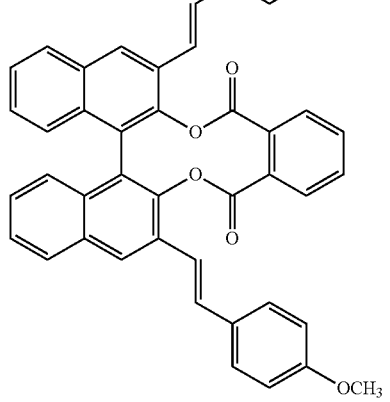

CD-14
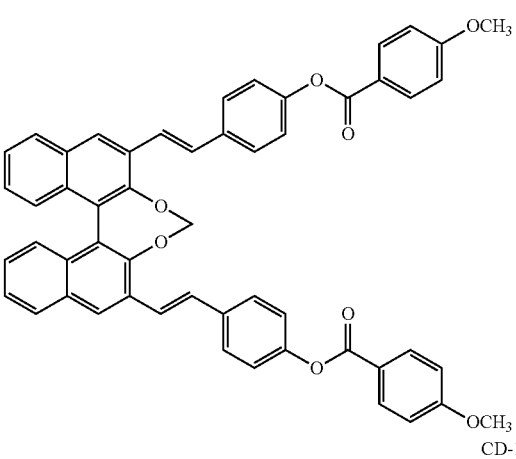

CD-15
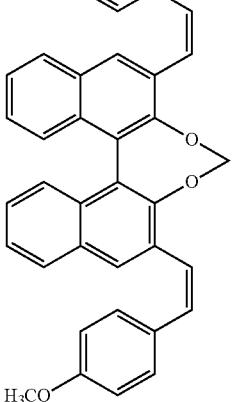

CD-16
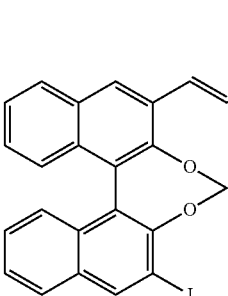

[Synthesis of Compounds CE-1 to CE-3 (Comparative Compounds)]

In addition, as comparative compounds, compounds CE-1 to CE-3 were synthesized.

The compound CE-1 was a compound disclosed in JP2004-250341A, and was synthesized according to the method disclosed in JP2004-186156A.

The compound CE-2 was a compound disclosed in JP2004-250341A, and was synthesized according to the method disclosed in the above reference.

The compound CE-3 was a compound described in Organic Letters. 2010; vol. 12; No. 8; pp. 1832 to 1835, and was synthesized according to the method described in the above reference.

The structures of the compounds CE-1 to CE-3, which are comparative compounds, are shown below.

CE-1

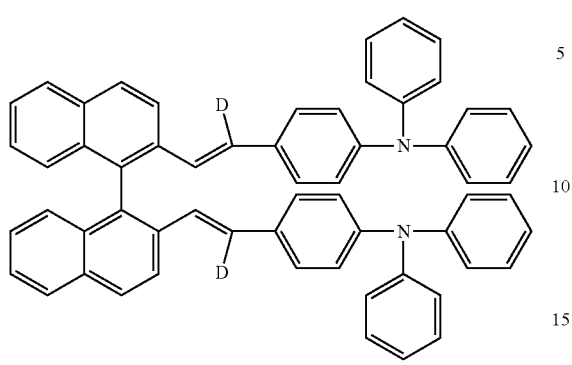

CE-2

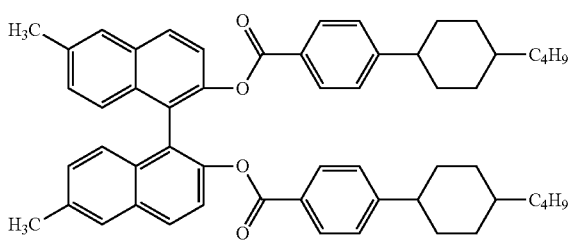

CE-3

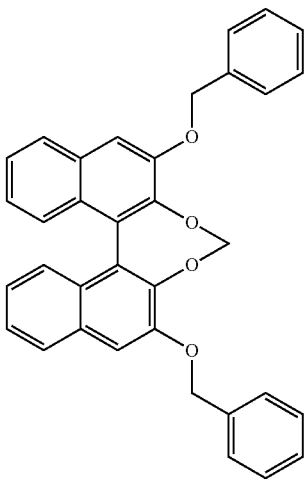

[Evaluation]
[Evaluation of Helical Twisting Power (HTP) and Rate of Change in HTP Caused by Exposure]

Various compositions for evaluation were prepared with the formulations shown below.

Any one of compounds CD-1 to CD-16, or CE-1 to CE-3: 5 parts by mass

Liquid crystalline compound LC-1 shown below: 100 parts by mass

Solvent (methyl ethyl ketone (MEK)): amount at which the concentration of solid contents of the composition is 30% by mass

LC-1

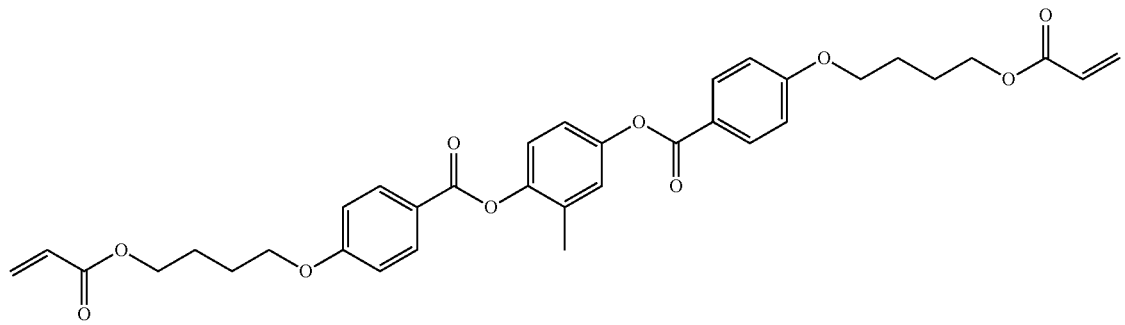

<Production of Liquid Crystal Layer 1>

A polyimide alignment film material SE-130 (manufactured by Nissan Chemical Corporation) was applied to a washed glass substrate to form a coating film. After firing the obtained coating film, the coating film was subjected to a rubbing treatment to produce a substrate with an alignment film.

40 μL of the above-described composition was spin-coated on the rubbing-treated surface of the alignment film under the conditions of 1500 rpm and 10 seconds, and then the substrate was heat-dried at 90° C. for 1 minute to form a composition layer.

Regarding the obtained composition layer, the central reflection wavelength was measured at room temperature (23° C.) using a microscope (ECLIPSE E600-POL manufactured by Nikon Corporation) and a spectrophotometer (UV-3100(PC) manufactured by Shimadzu Corporation), and HTP (initial HTP) was calculated according to the following expression.

HTP [μm$^{-1}$]=(average refractive index of liquid crystalline compound)/{(concentration (% by mass) of chiral compound with respect to liquid crystalline compound)×(central reflection wavelength)}

HTP was calculated on the assumption that the average refractive index of the liquid crystalline compound was 1.55.

Furthermore, after exposing the composition layer to light having a wavelength of 365 nm (exposure amount: 400 mJ/cm$^2$), the central reflection wavelength was measured again, and HTP after exposure was calculated in the same manner as the initial HTP using the above-described calculation expression. From the obtained initial HTP and HTP after exposure, the rate of change in HTP was calculated according to the following expression.

Rate of change in HTP [%]=|{(initial HTP)−(HTP after exposure)}/(initial HTP)×100|

The initial HTP and the rate of change in HTP were evaluated based on the following standard, respectively. In both standards, evaluation A is the most preferable. The results are shown in Table 1.

(Evaluation Standard of Initial HTP)

"A": initial HTP was 90 μm$^{-1}$ or more.
"B": initial HTP was 60 μm$^{-1}$ or more and less than 90 μm$^{-1}$.
"C": initial HTP was 30 μm$^{-1}$ or more and less than 60 μm$^{-1}$.
"D": initial HTP was 10 μm$^{-1}$ or more and less than 30 μm$^{-1}$.
"E": initial HTP was less than 10 μm$^{-1}$.

(Evaluation standard of rate of change in HTP)

"A": rate of change in HTP was 90% or more.
"B": rate of change in HTP was 65% or more and less than 90%.
"C": rate of change in HTP was 40% or more and less than 65%.
"D": rate of change in HTP was 30% or more and less than 40%.
"E": rate of change in HTP was 20% or more and less than 30%.
"F": rate of change in HTP was less than 20%.

In Table 1, the column of "Position of substituent represented by General Formula (2)" indicates a position having the substituent represented by General Formula (2), among $X^1$ to $X^4$ in General Formula (1).

In addition, the column "$A^1$" indicates whether or not $A^1$ in General Formula (2) is an aromatic hydrocarbon ring group. Specifically, a case where $A^1$ in General Formula (2) represents an aromatic hydrocarbon ring group is indicated as "A", and a case where $A^1$ in General Formula (2) does not represent an aromatic hydrocarbon ring group is indicated as "B".

In addition, the column "m" indicates whether or not m in General Formula (2) is 1 or 2. Specifically, a case where m in General Formula (2) is 1 or 2 is indicated as "A", and a case where m in General Formula (2) is 0 is indicated as "B".

In addition, the column "General Formula (3)" indicates whether or not $X^5$ and $X^6$ in General Formula (1) are the substituent represented by General Formula (3). Specifically, a case where both $X^5$ and $X^6$ represent the substituent represented by General Formula (3) is indicated as "A", and a case where both $X^5$ and $X^6$ do not represent the substituent represented by General Formula (3) is indicated as "B".

In addition, the column "cis-trans" indicates whether the arrangement of the site represented by -$A^1$-($Z^1$-$A^2$)$_m$-$R^1$ and the bonding position represented by *- in —CH=CH— of General Formula (2) is a cis-form or a trans-form (in other words, whether the bonding of the binaphthyl skeleton of General Formula (1) and the site represented by -$A^1$-($Z^1$-$A^2$)$_m$-$R^1$ of General Formula (2) in —CH=CH— of General Formula (2) is a cis-form or a trans-form). Specifically, a case of being a cis-form is indicated as "c", and a case of being a trans-form is indicated as "t".

TABLE 1

| | | Structure of compound represented by General Formula (1) | | | | | | | Evaluation | |
| --- | --- | --- | --- | --- | --- | --- | --- | --- | --- | --- |
| | Type of compound | Position of substituent represented by General Formula (2) | $A^1$ | | m | | General Formula (3) | cis-trans | Initial HTP | Rate of change in HTP |
| Example 1 | CD-1 | $X^1,X^2$ | $X^1$:A | $X^2$:A | $X^1$:B | $X^2$:B | A | $X^1$:t $X^2$:t | C | B |
| Example 2 | CD-2 | $X^1,X^2$ | $X^1$:A | $X^2$:A | $X^1$:B | $X^2$:B | B | $X^1$:t $X^2$:t | D | B |
| Example 3 | CD-3 | $X^1,X^2$ | $X^1$:A | $X^2$:A | $X^1$:B | $X^2$:B | B | $X^1$:t $X^2$:t | D | B |
| Example 4 | CD-4 | $X^1,X^2$ | $X^1$:A | $X^2$:A | $X^1$:A | $X^2$:A | B | $X^1$:t $X^2$:t | B | C |
| Example 5 | CD-5 | $X^1,X^2$ | $X^1$:A | $X^2$:A | $X^1$:A | $X^2$:A | B | $X^1$:t $X^2$:t | B | C |
| Example 6 | CD-6 | $X^1,X^2$ | $X^1$:B | $X^2$:B | $X^1$:B | $X^2$:B | B | $X^1$:t $X^2$:t | D | E |
| Example 7 | CD-7 | $X^1,X^2$ | $X^1$:B | $X^2$:B | $X^1$:A | $X^2$:A | B | $X^1$:t $X^2$:t | C | E |
| Example 8 | CD-8 | $X^1,X^2$ | $X^1$:B | $X^2$:A | $X^1$:B | $X^2$:B | B | $X^1$:t $X^2$:c | E | A |
| Example 9 | CD-9 | $X^1,X^2$ | $X^1$:B | $X^2$:A | $X^1$:A | $X^2$:A | B | $X^1$:t $X^2$:c | D | A |
| Example 10 | CD-10 | $X^1$ | $X^1$:A | | $X^1$:A | | B | $X^1$:t | E | E |
| Example 11 | CD-11 | $X^3,X^4$ | $X^3$:A | $X^4$:A | $X^3$:B | $X^4$:B | A | $X^3$:t $X^4$:t | A | C |
| Example 12 | CD-12 | $X^3,X^4$ | $X^3$:A | $X^4$:A | $X^3$:B | $X^4$:B | B | $X^3$:t $X^4$:t | B | C |

TABLE 1-continued

| | | Structure of compound represented by General Formula (1) | | | | | | Evaluation | |
|---|---|---|---|---|---|---|---|---|---|
| | Type of compound | Position of substituent represented by General Formula (2) | $A^1$ | m | General Formula (3) | cis-trans | | Initial HTP | Rate of change in HTP |
| Example 13 | CD-13 | $X^3, X^4$ | $X^3$:A $X^4$:A | $X^3$:B $X^4$:B | B | $X^3$:t $X^4$:t | | B | C |
| Example 14 | CD-14 | $X^3, X^4$ | $X^3$:A $X^4$:A | $X^3$:A $X^4$:A | B | $X^3$:t $X^4$:t | | A | D |
| Example 15 | CD-15 | $X^3, X^4$ | $X^3$:A $X^4$:A | $X^3$:B $X^4$:B | B | $X^3$:c $X^4$:c | | D | A |
| Example 16 | CD-16 | $X^3$ | $X^3$:A | $X^3$:B | B | $X^3$:t | | E | E |
| Comparative example 1 | CE-1 | — | — | — | — | — | | C | F |
| Comparative example 2 | CE-2 | — | — | — | — | — | | C | F |
| Comparative example 3 | CE-3 | — | — | — | — | — | | C | F |

From the results in Table 1, it was confirmed that the compounds of Examples were excellent in the rate of change in HTP caused by exposure.

In addition, from the comparison between Example 4 and Example 10 and the comparison between Example 12 and Example 16, in a case where, in General Formula (1), $X^1$ and $X^2$ represent the substituent represented by General Formula (2), or $X^3$ and $X^4$ represent the substituent represented by General Formula (2), it was confirmed that both the initial HTP and the rate of change in HTP were superior.

In addition, from the comparison between Example 1 and Example 11, and Example 2 and Examples 12 and 13, and the comparison between Example 4 and Example 14, in a case where, in General Formula (1), $X^1$ and $X^2$ represent the substituent represented by General Formula (2), it was confirmed that the rate of change in HTP was superior.

In addition, from the comparison between Example 1 and Example 11, the comparison between Example 2 and Examples 12 and 13, and the comparison between Example 4 and Example 14, in a case where, in General Formula (1), $X^3$ and $X^4$ represent the substituent represented by General Formula (2), it was confirmed that the initial HTP was superior.

In addition, from the comparison between Example 4 and Example 7, and the comparison between Example 2 and Example 6, in a case where, in General Formula (2), $A^1$ represents an aromatic hydrocarbon ring group, it was confirmed that the rate of change in HTP was superior.

In addition, from the comparison between Examples 4 and 5 and Examples 2 and 3, the comparison between Example 9 and Example 8, and the comparison between Example 14 and Example 12, in a case where, in General Formula (2), m represents 1 or 2, it was confirmed that the initial HTP was superior.

In addition, the comparison between Example 8 and Example 2, the comparison between Example 9 and Example 4, and the comparison between Example 15 and Example 12, in a case where, in General Formula (2), the site represented by $-A^1-(Z^1-A^2)_m-R^1$ and the bonding position represented by *- are arranged in a cis-form in —CH═CH— (in other words, in a case where the binaphthyl skeleton of General Formula (1) and the site represented by $-A^1-(Z^1-A^2)_m-R^1$ of General Formula (2) is a cis-form in —CH═CH— of General Formula (2)), it was confirmed that the rate of change in HTP was superior.

In addition, from the comparison between Example 1 and Example 2, and the comparison between Example 11 and Example 12, in a case where $R^5$ or $R^6$ is the substituent represented by General Formula (3), it was confirmed that the initial HTP was superior.

[Production of Reflective Film]

[Preparation of Liquid Crystal Composition]

A liquid crystal composition was prepared with the formulation shown below.

Compound CD-1: 5 parts by mass

Liquid crystalline compound LC-1 shown above: 100 parts by mass

Surfactant S-1 shown below: 0.1 parts by mass

IRGACURE 907 (manufactured by BASF): 3 parts by mass

Solvent (methyl ethyl ketone/cyclohexanone=90:10 (mass ratio)): amount at which the concentration of solid contents of the composition is 30% by mass The surfactant S-1 is a compound described in JP5774518B, and has the following structure.

(S-1)

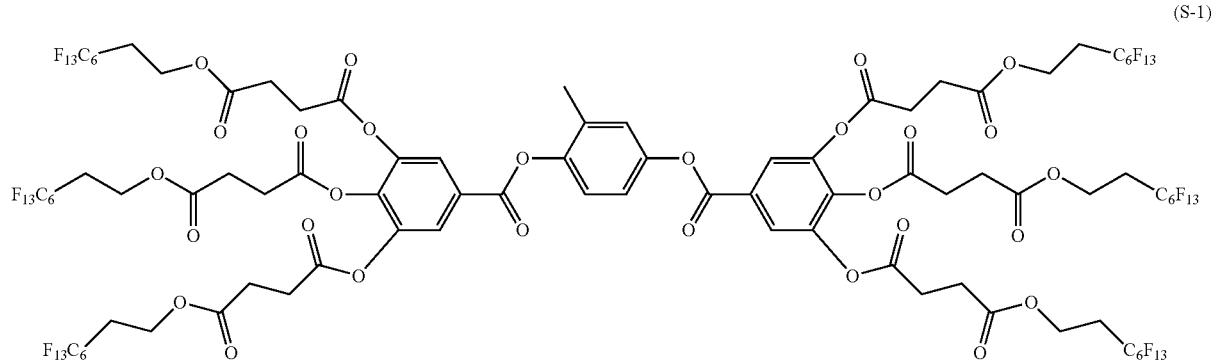

<Production of Reflective Film>

A polyimide alignment film material SE-130 (manufactured by Nissan Chemical Corporation) was applied to a washed glass substrate to form a coating film. After firing the obtained coating film, the coating film was subjected to a rubbing treatment to produce a substrate with an alignment film. 40 μL of the above-described liquid crystal composition was spin-coated on the rubbing-treated surface of the alignment film under the conditions of a rotation speed of 1500 rpm for 10 seconds to form a composition layer. Thereafter, the composition layer was dried (aged) at 90° C. for 1 minute, thereby aligning the liquid crystalline compound in the composition layer (in other words, obtaining a composition layer in a state of the cholesteric liquid crystalline phase).

Next, the composition layer in which the liquid crystalline compound had been aligned was irradiated with light, which is emitted from a light source (2UV Transilluminator manufactured by UVP Inc.) and has a wavelength of 365 nm, at an irradiation intensity of 4 mW/cm² for 10 seconds through a mask having an opening portion (corresponding to the treatment of changing HTP of CD-1). Due to the difference between the opening portion and the non-opening portion of the mask, the composition layer was in a state of having a portion irradiated with light having a wavelength of 365 nm and a portion not irradiated with light.

Subsequently, in a state of removing the mask, the composition layer was subjected to a curing treatment by irradiation with ultraviolet rays (310 nm) at an irradiation amount of 500 mJ/cm² under a nitrogen atmosphere at 25° C., thereby obtaining a reflective film (corresponding to a layer obtained by immobilizing the cholesteric liquid crystalline phase).

In the obtained reflective film, it was found that the selective reflection wavelengths differed between the portion irradiated with light having a wavelength of 365 nm and the portion not irradiated (that the helical pitches of the cholesteric layer differed therebetween).

What is claimed is:

1. A compound represented by General Formula (1),

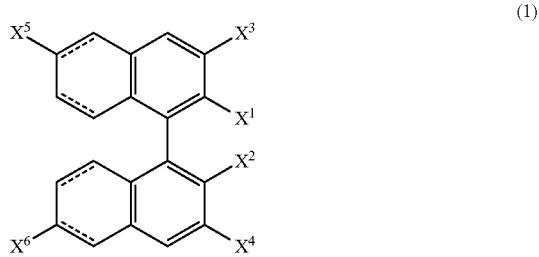

(1)

in General Formula (1), a portion where a solid line and a broken line are parallel to each other represents a single bond or a double bond, in General Formula (1), $X^1$ to $X^6$ each independently represent a hydrogen atom or a substituent, at least two of $X^1$, $X^2$, $X^3$, or $X^4$ represents a substituent represented by General Formula (2), and $X^1$ and $X^2$ are each the substituent represented by General Formula (2), or $X^1$ and $X^2$ are linked to each other to form a ring and $X^3$ and $X^4$ are each the substituent represented by General Formula (2),

*—CH=CH-A¹-(Z¹-A²)$_m$-R¹  (2)

in General Formula (2), $A^1$ represents a hydrocarbon ring group, $A^2$ represents a hydrocarbon ring group or a heterocyclic group, $R^1$ represents a hydrogen atom or a substituent, $Z^1$ represents a single bond, —O—, —S—, —CH₂O—, —CO—, —COO—, —CO—S—, —O—CO—O—, —CO—NH—, —NR$^A$—, —CH₂CH₂—, —CH₂S—, —CF₂O—, —CF₂S—, —CH=CH—COO—, —CH=CH—OCO—, —OCO—C(CN)=CH—, —COO—CH₂CH₂—, —OCO—CH₂CH₂—, —COO—CH₂—, —OCO—CH₂—, —CH=CH—, —N=N—, —CH=N—N=CH—, —CF=CF—, —C≡CCOO—, or —C≡C—, where $R^A$ represents a hydrogen atom or an alkyl group, m represents an integer of 0 to 2,

* represents a bonding position to a binaphthyl skeleton in General Formula (1), in a case where m is 2, a plurality of $Z^1$'s may be the same or different from each other and a plurality of $A^2$'s may be the same or different from each other, and a plurality of substituents represented by General Formula (2) may be the same or different from each other, and the compound represented by General Formula (1) satisfies all of the following requirements (A) and (B), requirement (A): in General Formula (2), in a case where $R^1$ is a substituent represented by —NR$^B$R$^C$, at least one of $R^B$ or $R^C$ represents a hydrogen atom or an alkyl group, and requirement (B): in a case where two or more of $X^1$ to $X^4$ represent the substituent represented by General Formula (2), a plurality of $R^1$'s do not linked to each other to form a ring, and a plurality of $A^1$'s do not linked to each other to form a ring and a plurality of $A^2$'s do not linked to each other to form a ring.

2. The compound according to claim 1, wherein, in General Formula (1), $X^3$ and $X^4$ each independently represent the substituent represented by General Formula (2).

3. The compound according to claim 1, wherein, in General Formula (1), $X^1$ and $X^2$ each independently represent the substituent represented by General Formula (2).

4. The compound according to claim 1, wherein, in General Formula (2), $A^1$ represents an aromatic hydrocarbon ring group.

5. The compound according to claim 1, wherein, in General Formula (2), m represents 1 or 2.

6. The compound according to claim 1, wherein, in General Formula (1), $X^5$ and $X^6$ each independently represent a substituent represented by General Formula (3),

*—Z²-(A³-Z³)$_n$—R²  (3)

in General Formula (3), $A^3$ represents a hydrocarbon ring group or a heterocyclic group, $R^2$ represents a sub stituent, $Z^2$ and $Z^3$ each independently represent a single bond, —O—, —S—, —CH₂O—, —CO—, —COO—, —CO—S—, —O—CO—O—, —CO—NH—, —NLA—, —CH₂CH₂—, —CH₂S—, —CF₂O—, —CF₂S—, —CH=CH—COO—, —CH=CH—OCO—, —OCO—C(CN)=CH—, —COO—CH₂CH₂—, —OCO—CH₂CH₂—, —COO—CH₂—, —OCO—CH₂—, —CH=CH—, —N=N—, —CH=N—N=CH—, —C=N—, —CF=CF—, —C≡CCOO—, or —C≡C—, where $L_A$ represents a hydrogen atom or an alkyl group, n represents an integer of 0 to 2, \* represents a bonding position to the binaphthyl skeleton in General Formula (1), and in a case where n is 2, a plurality of $A^3$'s may be the same or different from each other and a plurality of $Z^3$'s may be the same or different from each other.

7. The compound according to claim 1, wherein, in General Formula (2), a site represented by $-A^1-(Z^1-A^2)_m-R^1$ and a bonding position represented by \*- are arranged in a cis-form in —CH═CH— of General Formula (2).

8. A liquid crystal composition comprising:

the compound according to claim 1; and a liquid crystalline compound.

9. The liquid crystal composition according to claim 8, wherein the liquid crystalline compound includes two or more polymerizable groups.

10. A cured product obtained by curing the liquid crystal composition according to claim 8.

11. An optically anisotropic body obtained by curing the liquid crystal composition according to claim 8.

12. A reflective film obtained by curing the liquid crystal composition according to claim 8.

\* \* \* \* \*